(12) United States Patent
Vogt et al.

(10) Patent No.: US 7,207,801 B2
(45) Date of Patent: Apr. 24, 2007

(54) ASSEMBLY FOR HANDLING AN IMPLANT

(75) Inventors: Martin Vogt, Sissach (CH); Hans Schurch, Titterten (CH)

(73) Assignee: Straumann Holding AG, Waldenburg (CH)

(*) Notice: Subject to any disclaimer, the term of this patent is extended or adjusted under 35 U.S.C. 154(b) by 449 days.

(21) Appl. No.: 10/472,494

(22) PCT Filed: Apr. 29, 2002

(86) PCT No.: PCT/CH02/00235

§ 371 (c)(1),
(2), (4) Date: Sep. 30, 2003

(87) PCT Pub. No.: WO02/087461

PCT Pub. Date: Nov. 7, 2002

(65) Prior Publication Data

US 2004/0096804 A1 May 20, 2004

(30) Foreign Application Priority Data

Apr. 27, 2001 (EP) .................. 01810419

(51) Int. Cl.
 *A61C 8/00* (2006.01)
(52) U.S. Cl. ...................... 433/173; 433/174
(58) Field of Classification Search ........ 433/172–174, 433/201.1; 206/63.5, 368, 369
See application file for complete search history.

(56) References Cited

U.S. PATENT DOCUMENTS

| 5,538,428 | A | * | 7/1996 | Staubli ................ 433/173 |
| 5,582,299 | A |   | 12/1996 | Lazzara et al. |
| 5,947,733 | A | * | 9/1999 | Sutter et al. ............ 433/173 |
| 5,996,779 | A | * | 12/1999 | Klardie et al. .......... 206/63.5 |
| 6,261,097 | B1 |   | 7/2001 | Schmutz et al. |
| 6,769,913 | B2 | * | 8/2004 | Hurson ................ 433/173 |

FOREIGN PATENT DOCUMENTS

| DE | 19731073 | 7/1997 |
| EP | 879024 | 8/1997 |

* cited by examiner

*Primary Examiner*—Cris Rodriguez
*Assistant Examiner*—Patrick J. Kilkenny
(74) *Attorney, Agent, or Firm*—Shoemaker and Mattare

(57) ABSTRACT

An assembly for handling a bone implant includes a transfer cap which can be snapped onto the implant, and an adapter which engages with the implant. The head of the implant has a polygonal socket, an outer implant shoulder, and a shoulder edge located beneath the shoulder, while the transfer cap has an elastic lip that snaps over the shoulder edge, and the adapter has a polygonal drive projection adapted to engage within the polygonal socket. The adapter also has a plug-type extension for attaching a screw-in instrument. When the transfer cap is snapped onto the implant and the adapter is inserted, the polygonal projection engages with the polygonal socket on the implant, while the plug-type extension of the adapter that projects through the transfer cap is located on the outside. The transfer cap and the adapter plugged therein are detachably connected to one another.

10 Claims, 25 Drawing Sheets

Figure 1A:
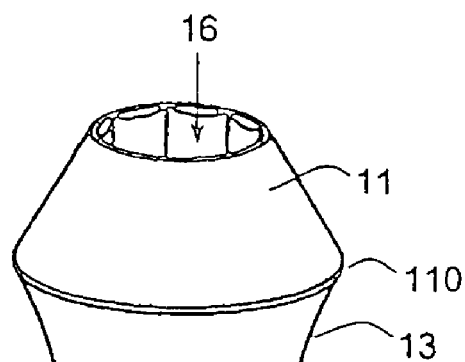

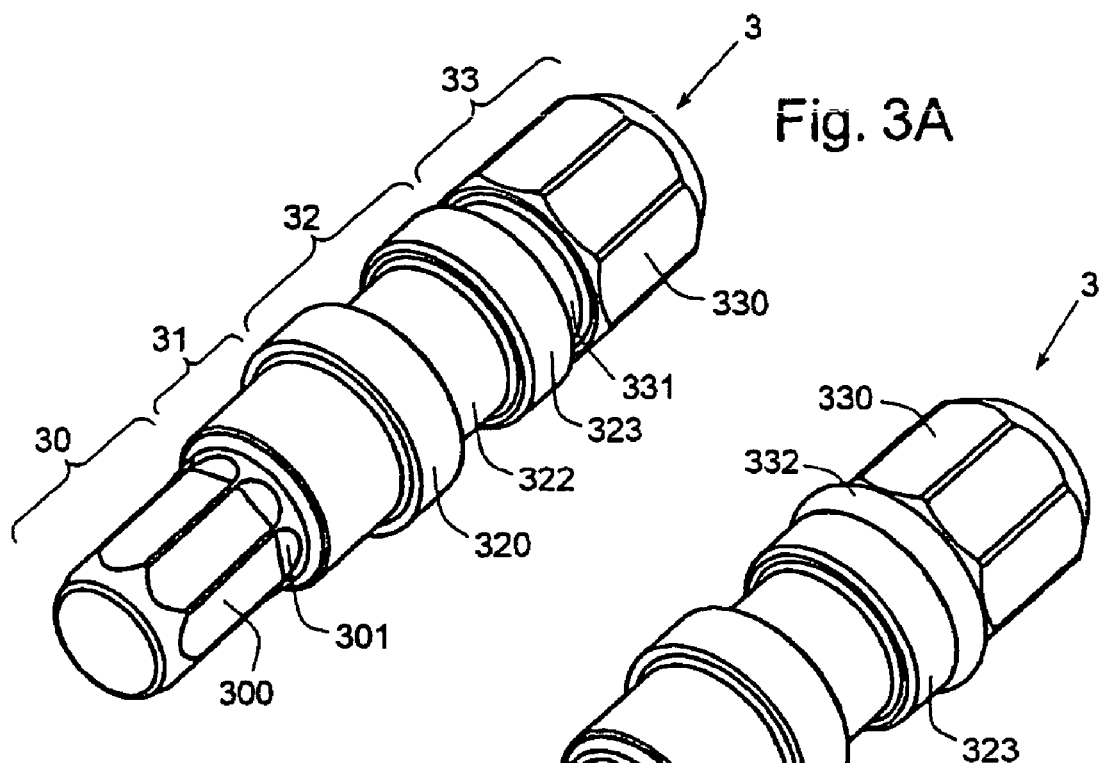
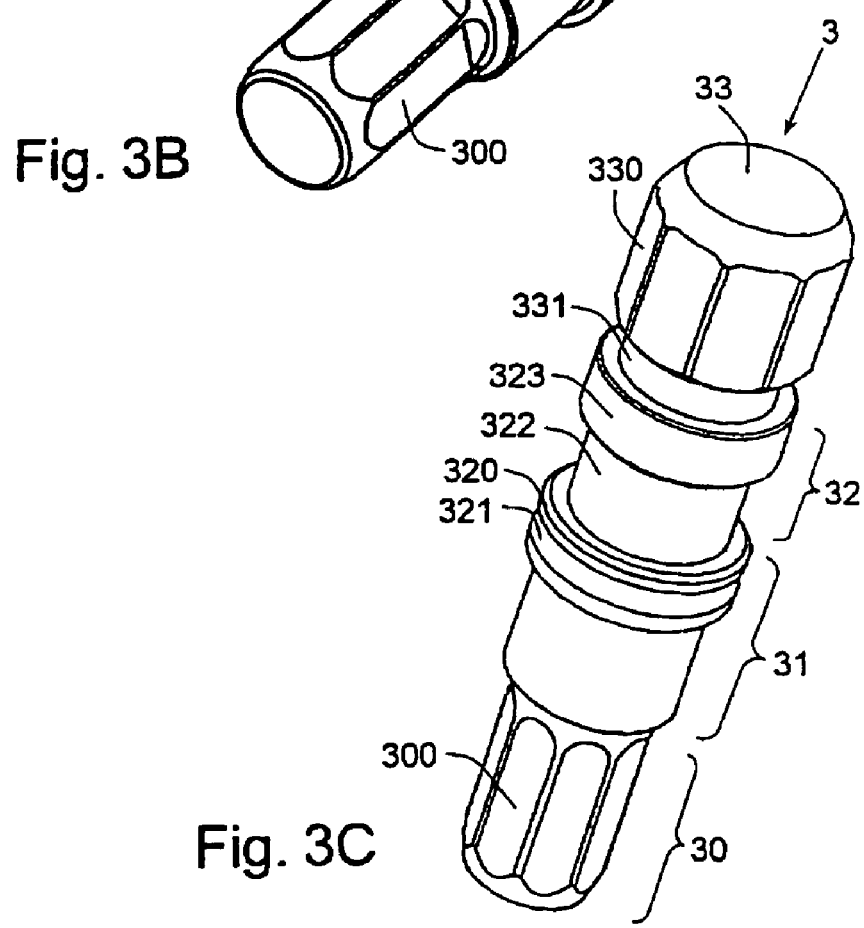

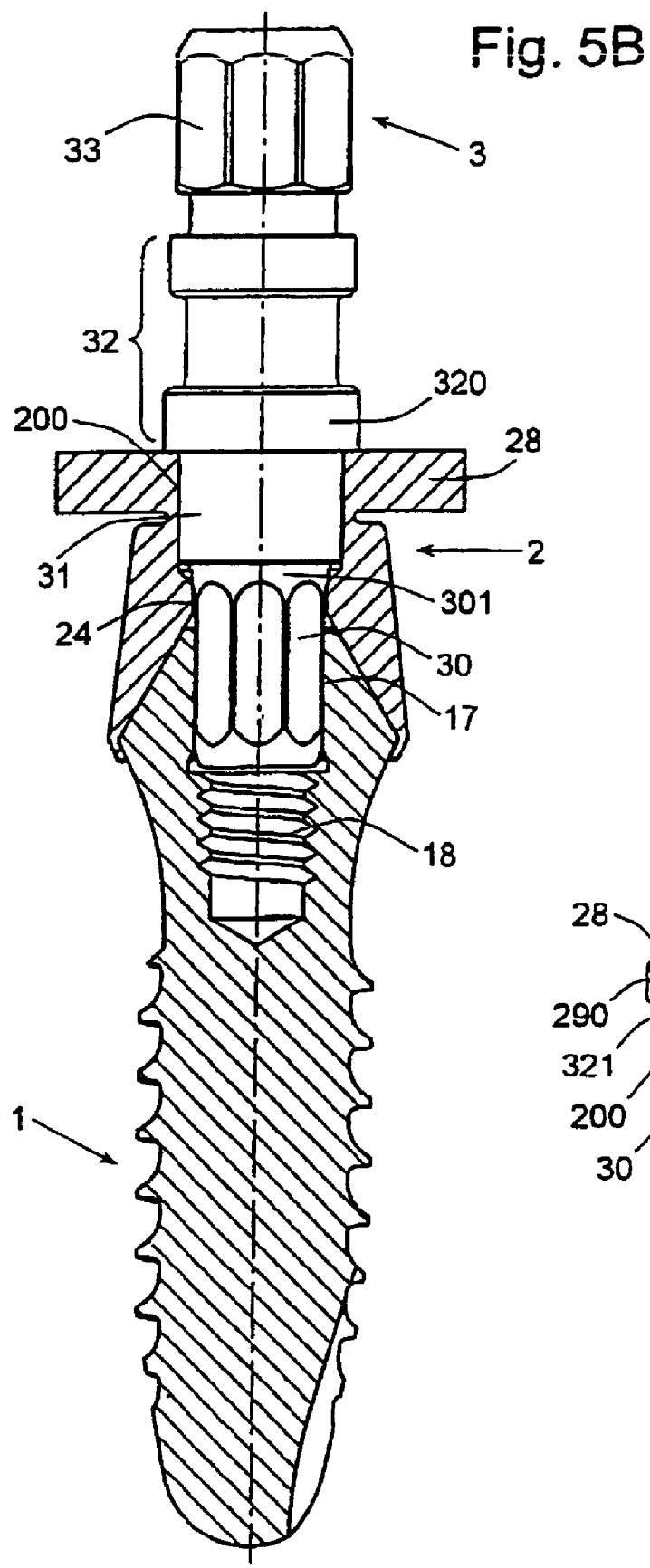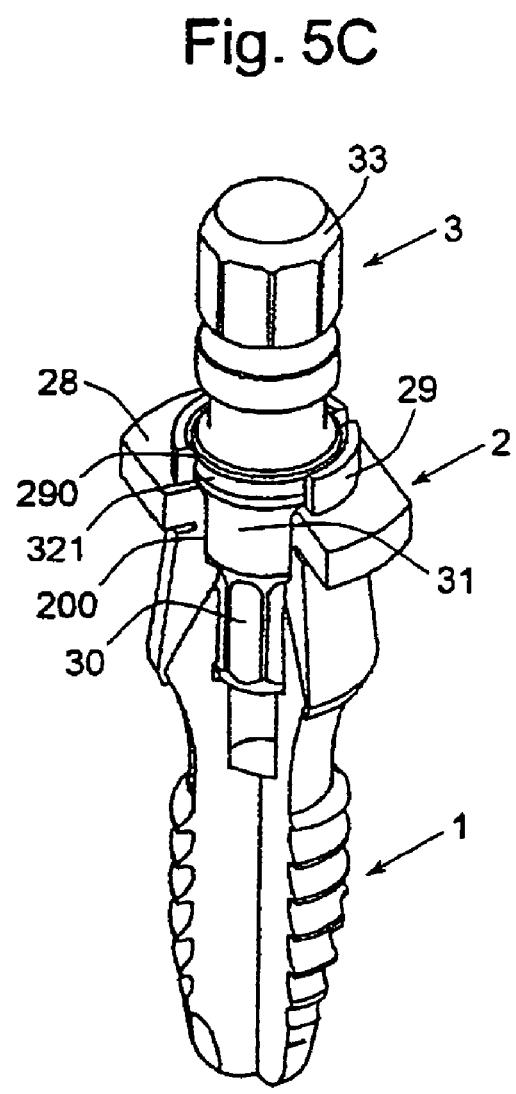

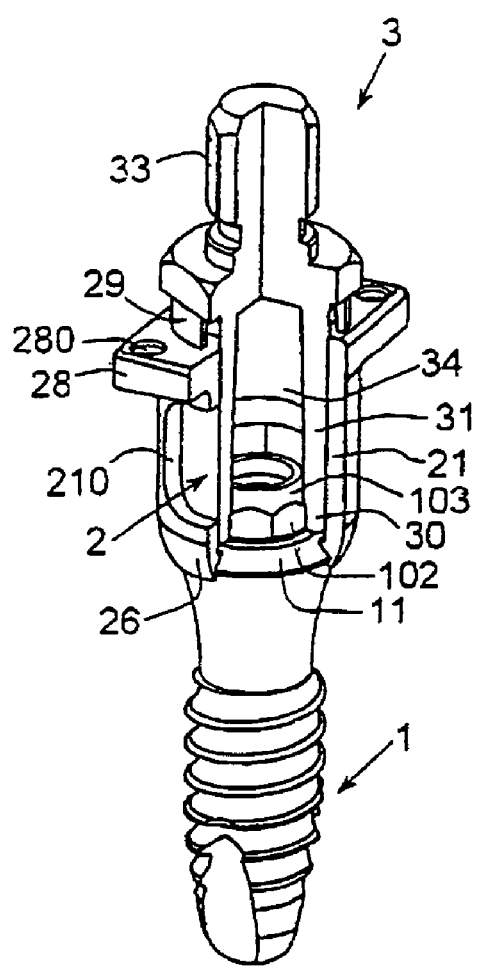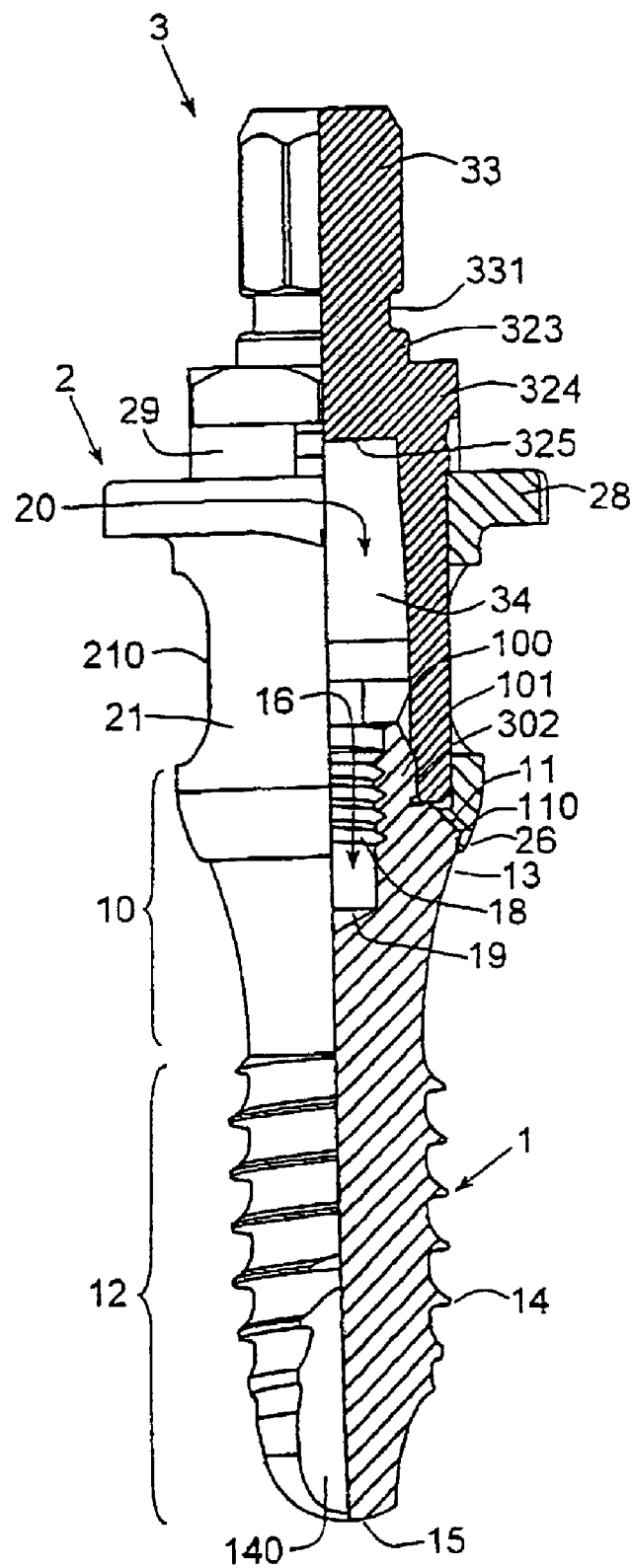
Fig. 6A
Fig. 6B

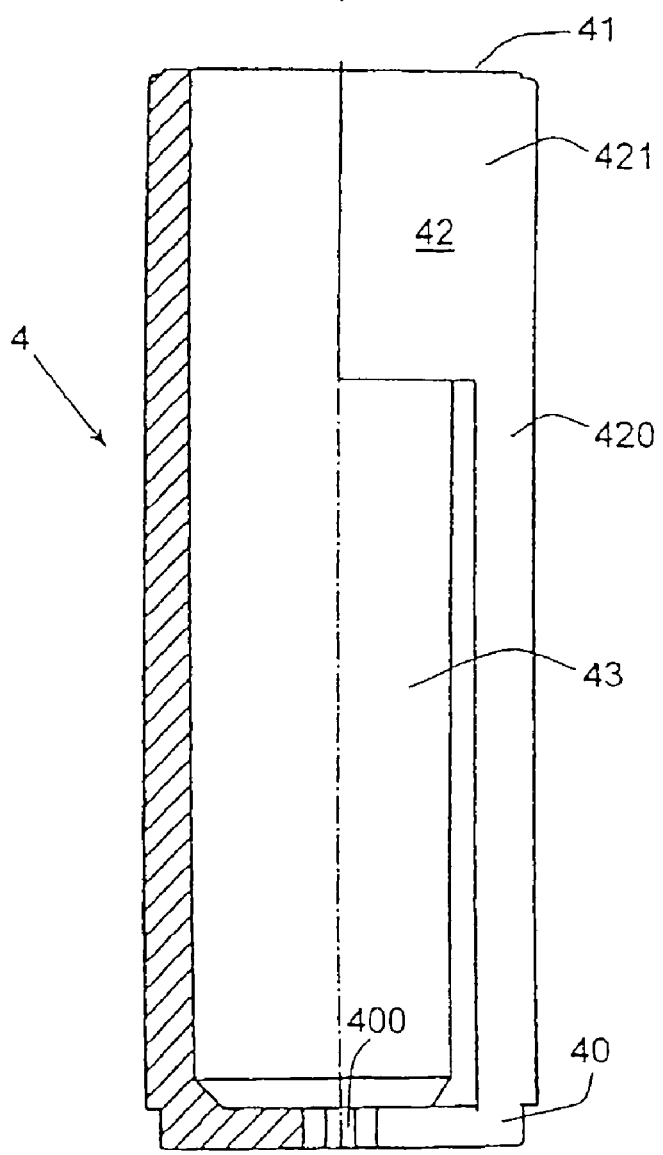

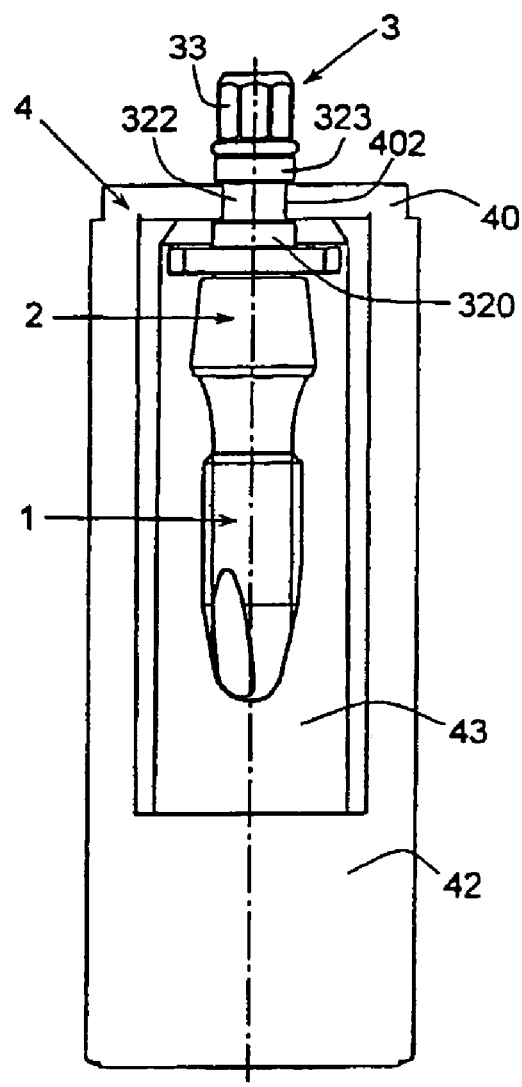
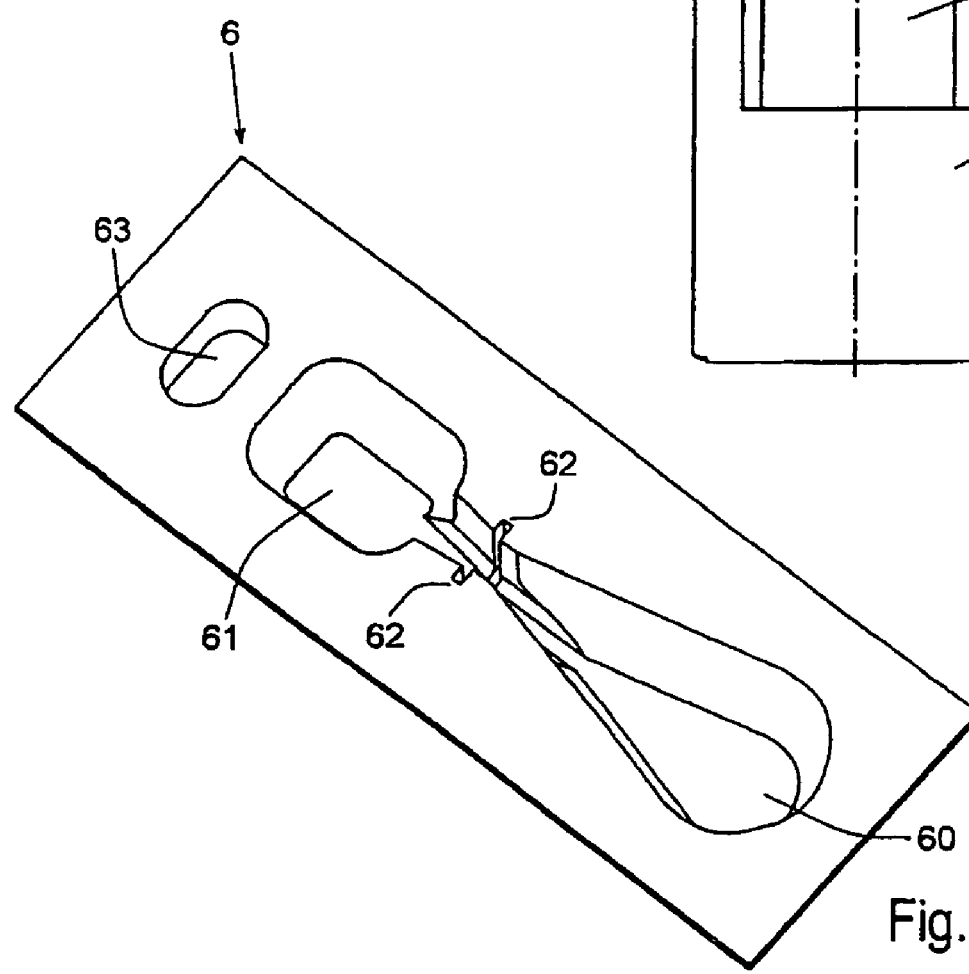

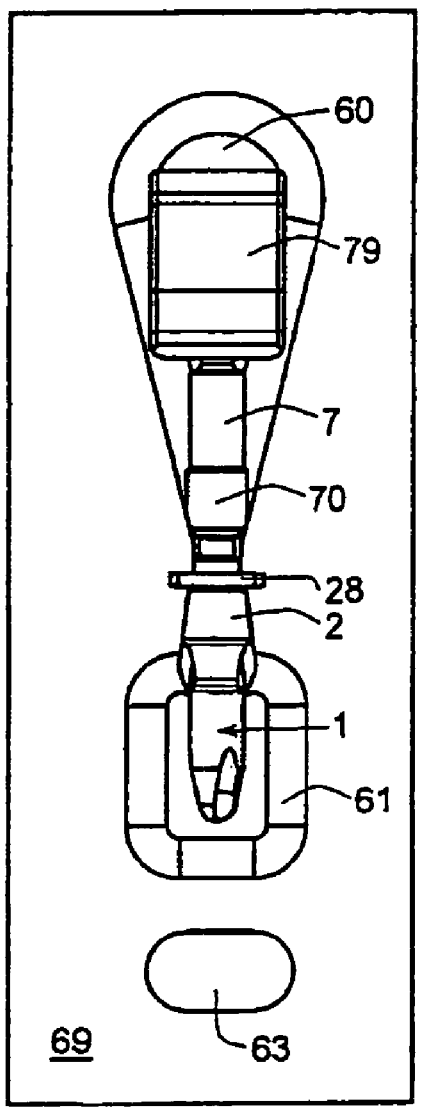
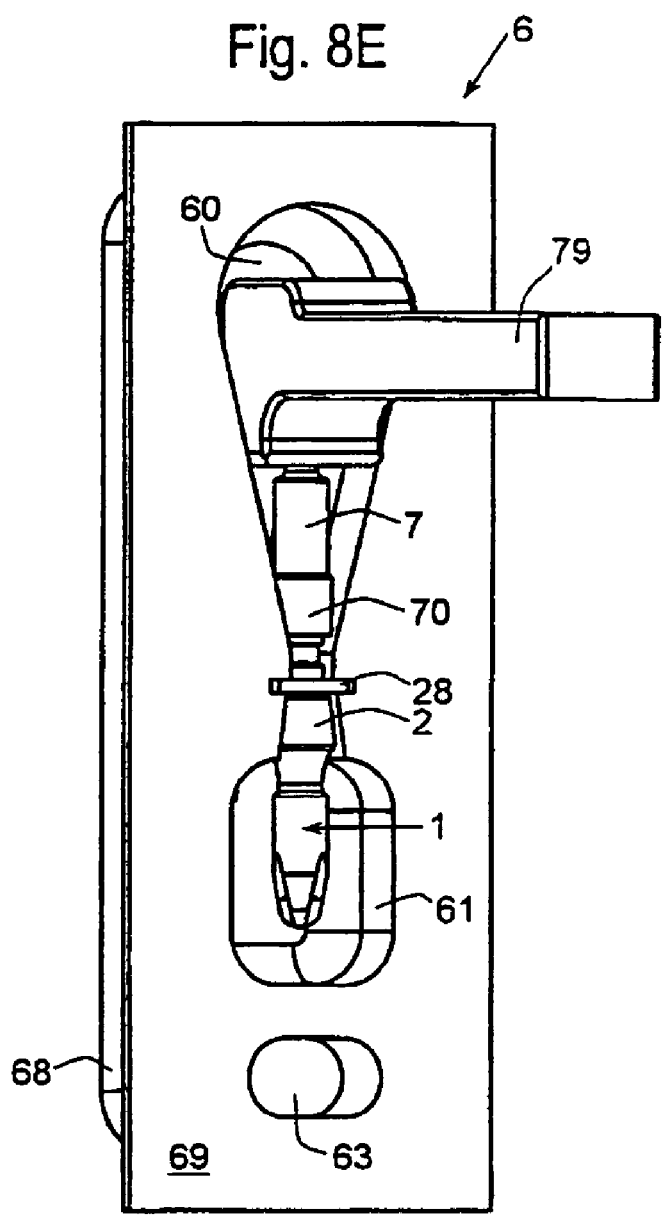
Fig. 8D
Fig. 8E

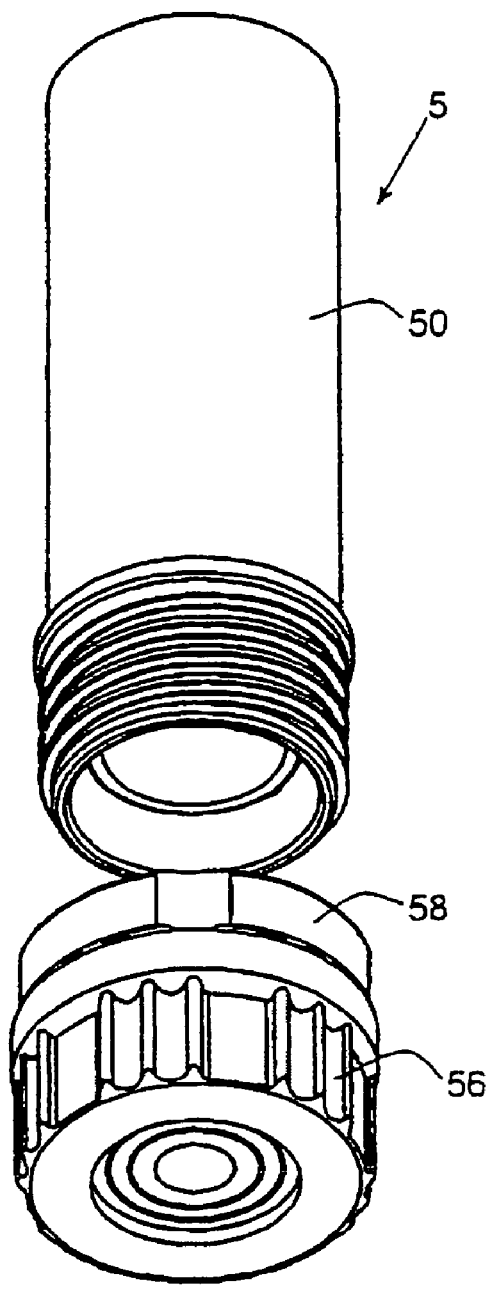
Fig. 9A
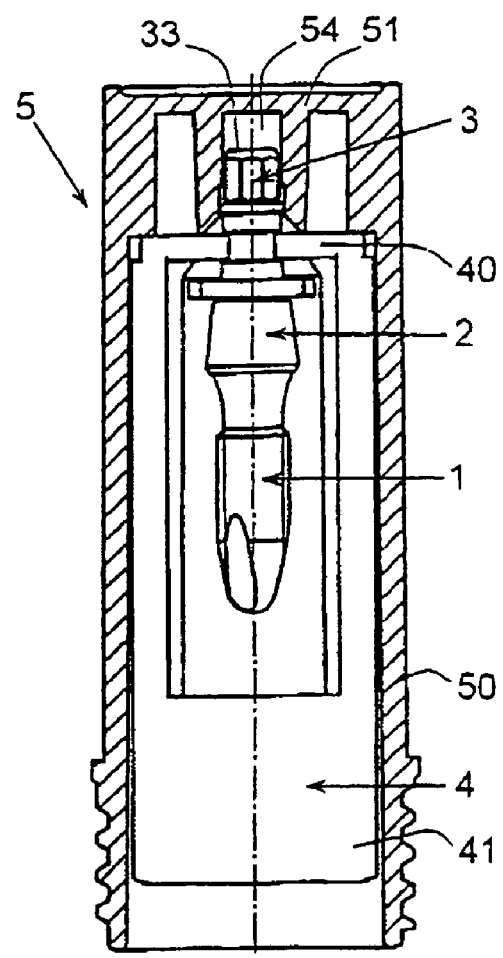
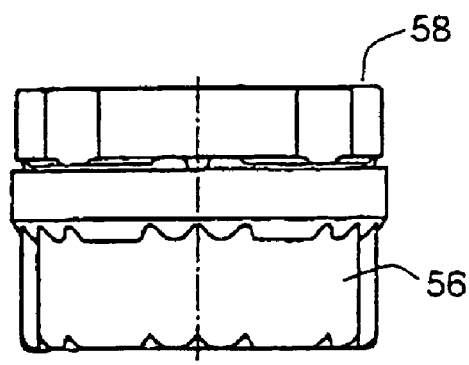
Fig. 10A

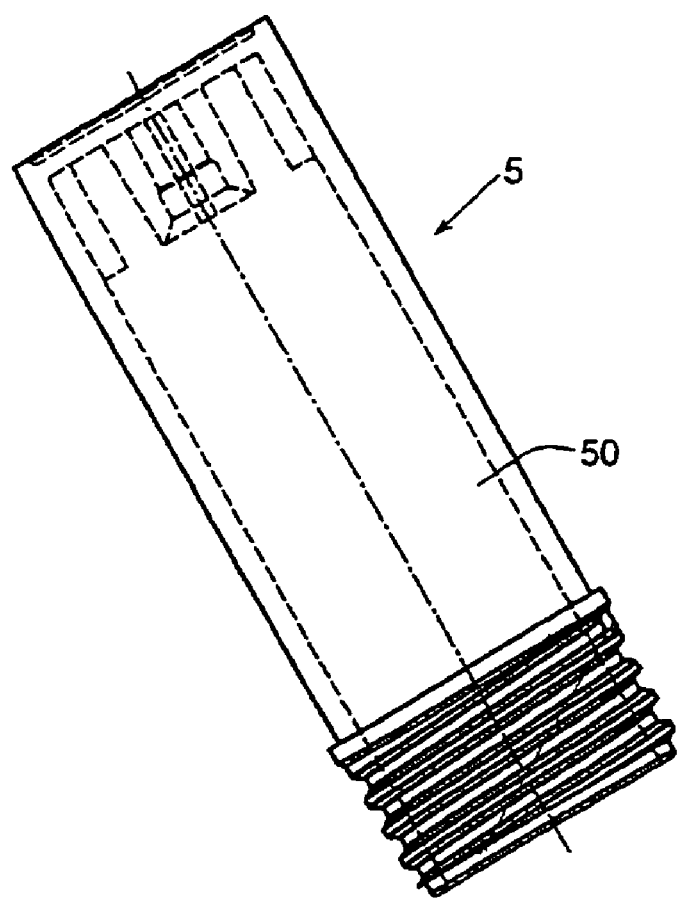
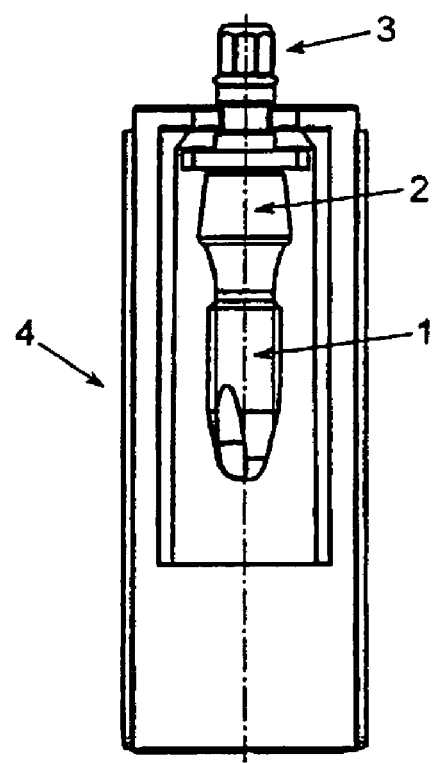
Fig. 11A

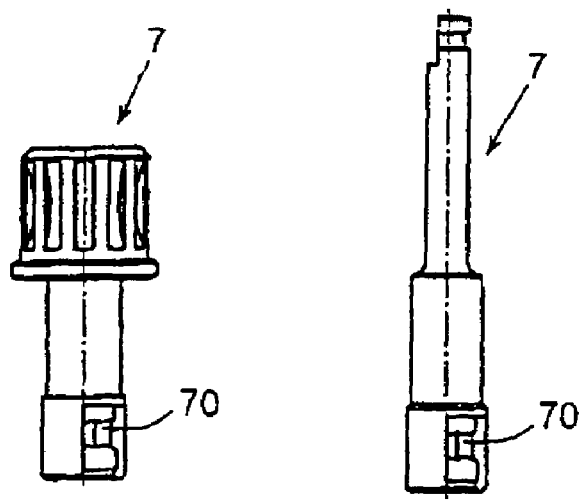
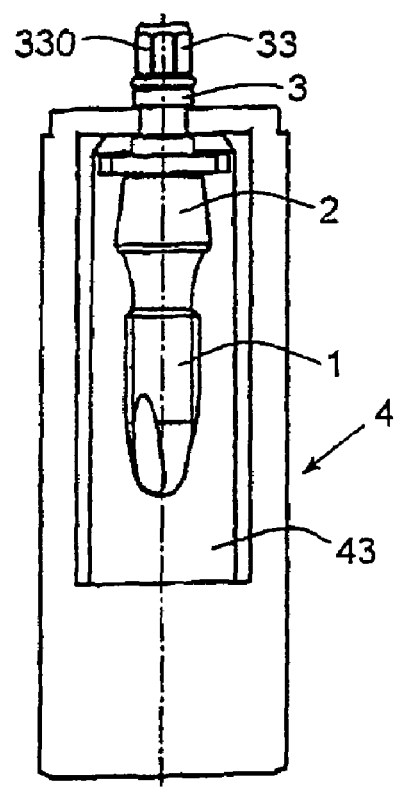
Fig. 11B
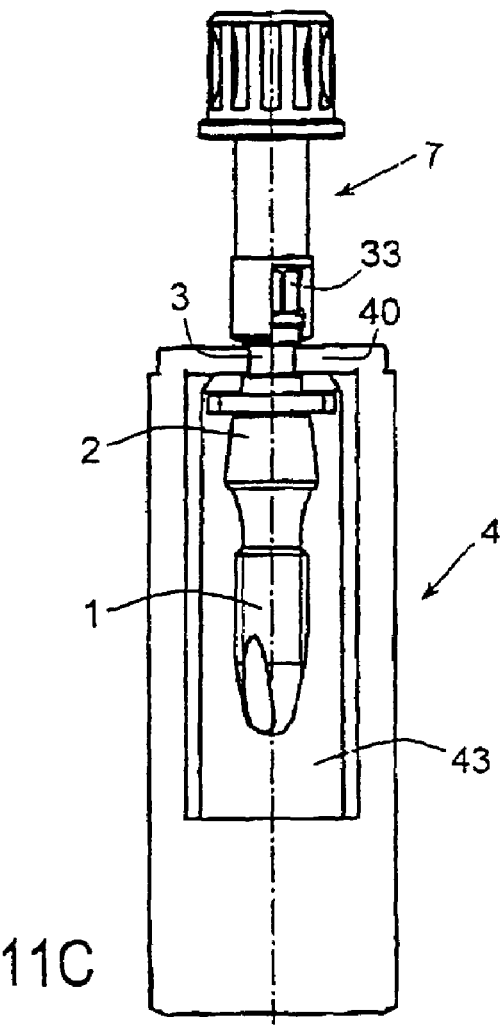
Fig. 11C

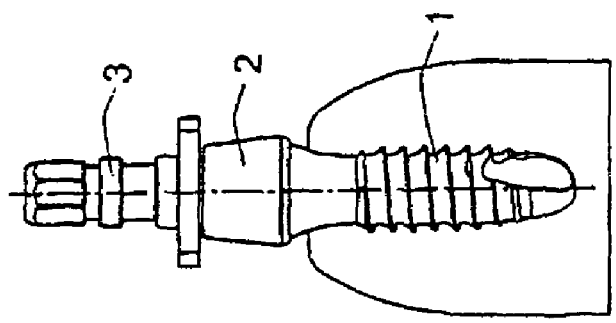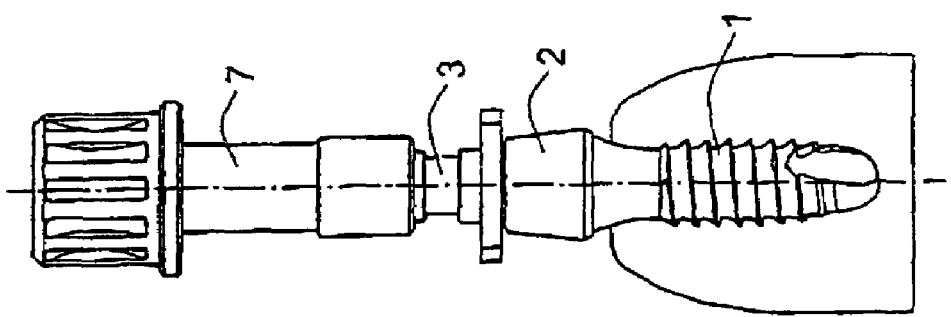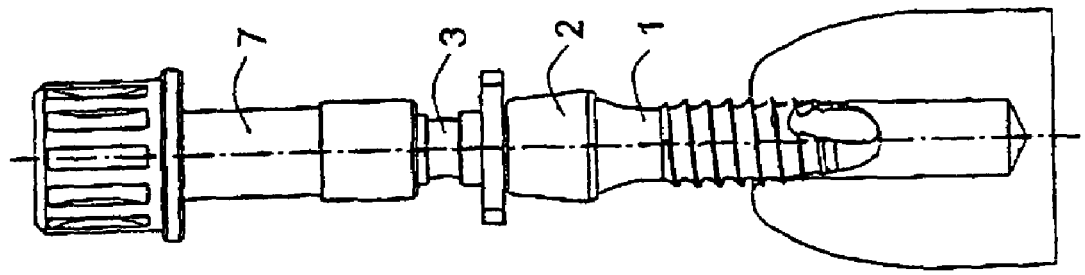

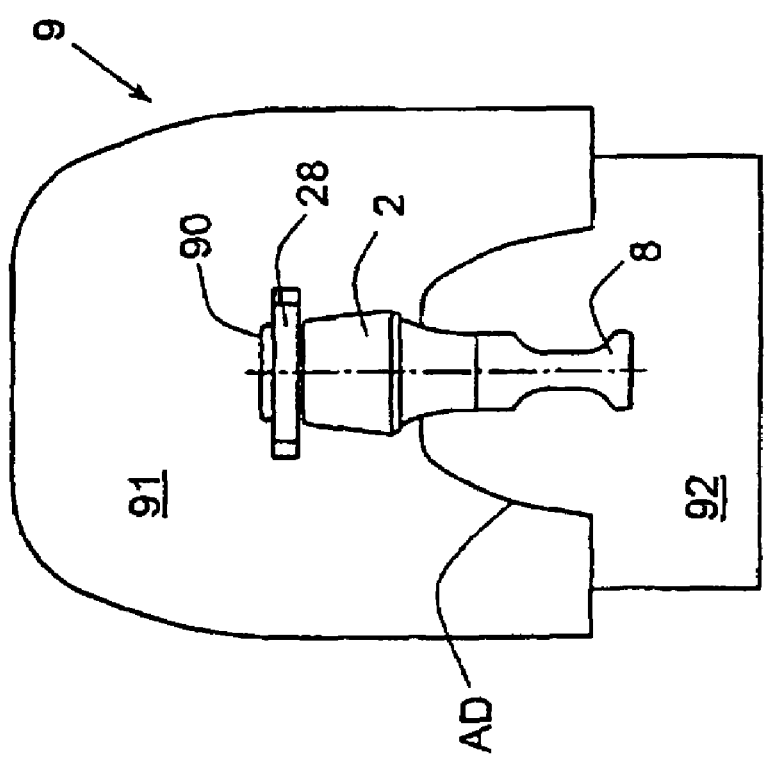
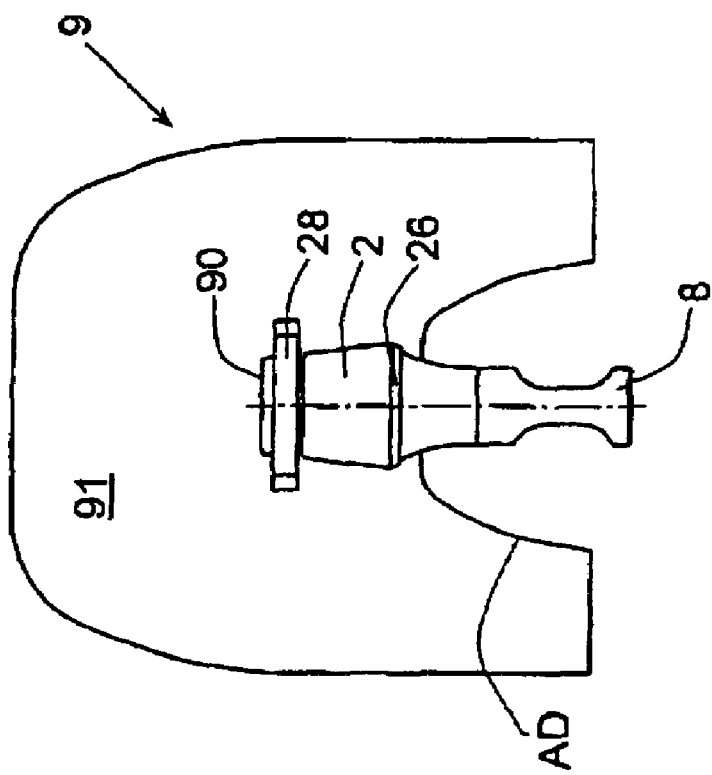

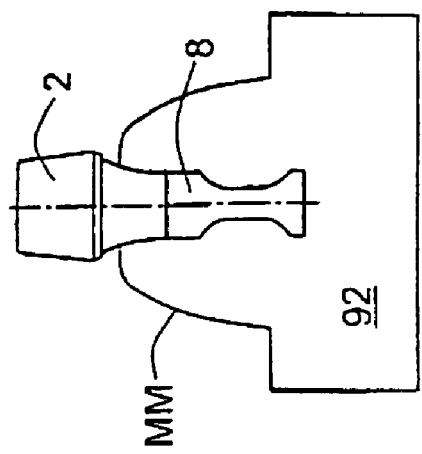
Fig. 12M
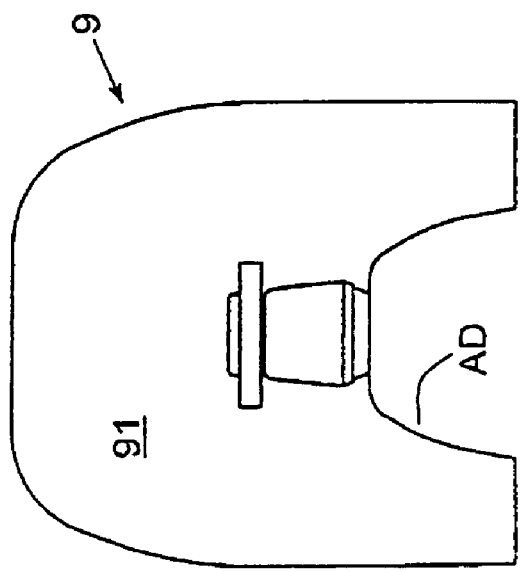
Fig. 12L
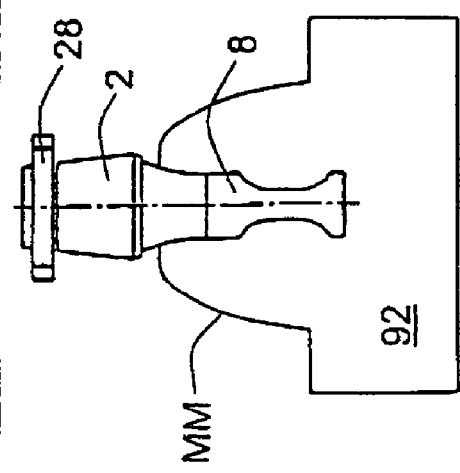
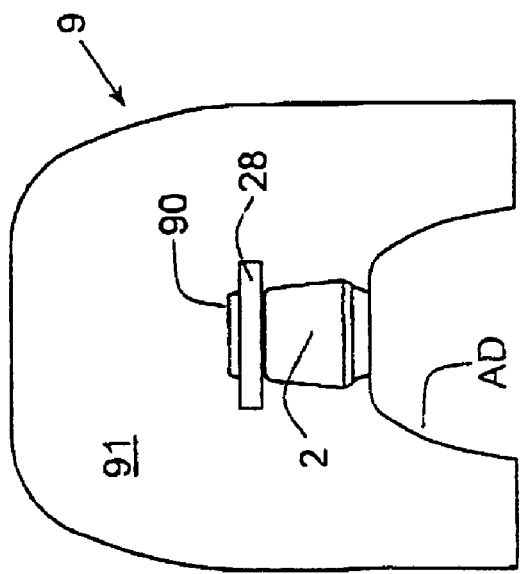
Fig. 12K
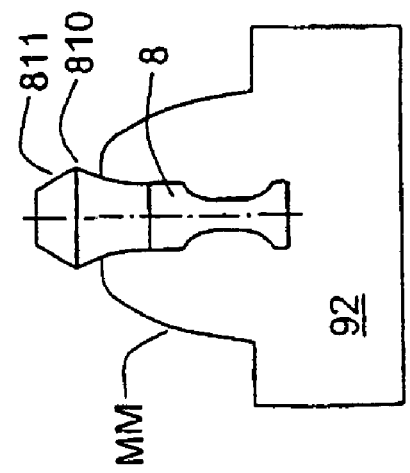

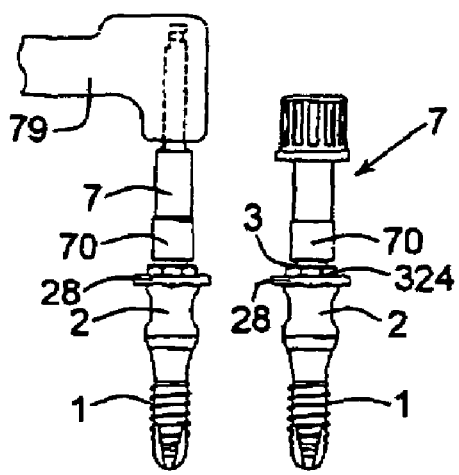
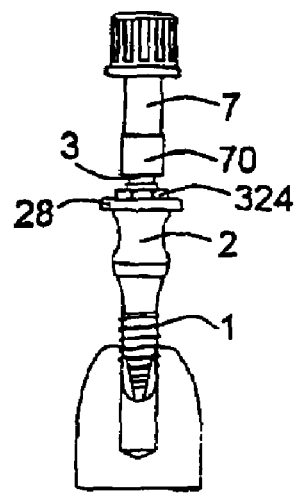
Fig. 13A  Fig. 13B
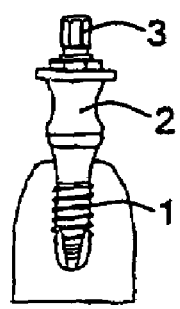
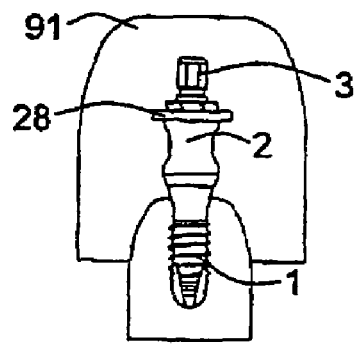
Fig. 13C  Fig. 13D
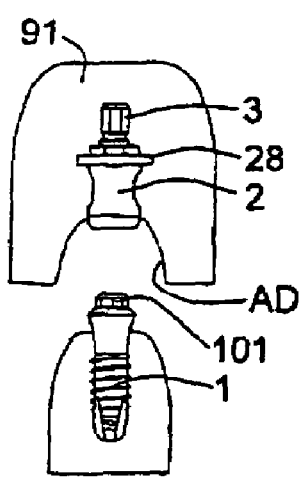
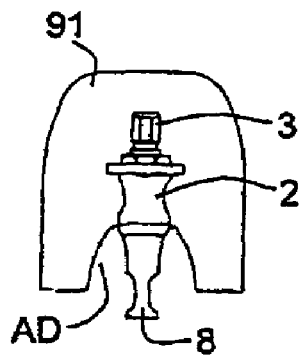
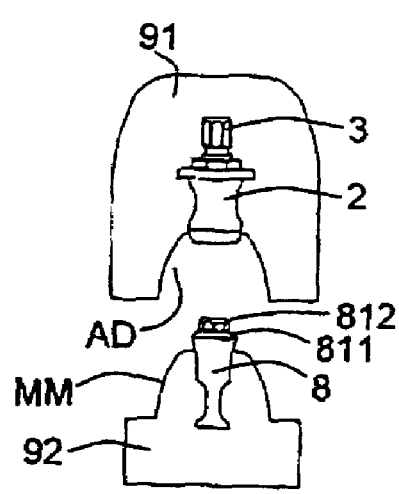
Fig. 13E  Fig. 13F  Fig. 13G

ASSEMBLY FOR HANDLING AN IMPLANT

FIELD OF APPLICATION OF THE INVENTION

The present invention relates to an arrangement for handling an implant which, on the implant head, has an axially emerging bore with a non-rotationally symmetrical inner contour, preferably an internal polygon. An internally threaded portion can be arranged inside the axial bore. The mouth of the axial bore is surrounded by an implant shoulder which forms the upper end of the implant. Such implants are used in the dental field, for example, and are intended to be inserted into a receiving bore formed beforehand in the jaw bone. Screw-type implants are screwed into an internally threaded bore formed beforehand in the bone or have a self-cutting external thread which, on being screwed into a prepared blind hole, itself generates the internal thread. By contrast, cylinder-type implants have no external thread and are pressed into a blind hole formed beforehand in the bone. The present invention relates principally to intraosseous dental implants of the screw type.

For transfer to the implant bed, and for screwing in the case of screw-type implants, the arrangement includes an adapter whose bottom shaft plugs into the non-rotationally symmetrical inner contour in the implant head in a complementary way. The upper continuation of the adapter has a non-rotationally symmetrical contour, preferably an external polygon, in order to attach a screwing-in instrument to it. The arrangement also comprises a cap which can be locked over the implant shoulder. To transport and store the implant, a container is provided in an extension of the arrangement. During the surgical operation, the implant can be removed from the container under sterile conditions, with the screwing-in instrument connected to the continuation of the adapter, and can then be introduced with this instrument into the receiving bore in the bone.

PRIOR ART

Various adapters are known for handling the aforementioned implant type; different impression caps exist for transferring the geometric contour in the environment of the implant fitted in the patient, and differently designed ampoules for storing such implants are available on the market.

WO 98/26726 proposes an adapter sleeve which bears on the edge of a through-bore in a dividing wall inside the sterile ampoule. In addition to retaining the implant in the sterile ampoule, the adapter sleeve is mainly provided for temporary connection between the implant and a manipulating member. The first end of the adapter sleeve is once again fitted in a releasable manner onto a plug-type extension of the positioned implant; the tip of the manipulating member can be releasably applied to the second end of the adapter sleeve. When the manipulating member is applied to the adapter sleeve already connected to the implant, said implant has been gripped. This results in a twin plug-in connection between implant, adapter sleeve and manipulating member, with which the implant can be transferred almost free of contact. When the manipulating member is released from the implant, only the plug-type connection between the implant and the manipulating member is undone. This adapter sleeve represents a further structural part and is not suitable for transmitting the torque generated when the implant is screwed in with a screwing-in instrument.

From U.S. Pat. No. 5,538,428 it is known to arrange an adapter between the lid of an ampoule and the implant stored therein, which adapter consists of a sleeve part and of a rotatable screw extending through the sleeve part. At the bottom, facing toward the implant shoulder, the sleeve part has an internal polygon for receiving the complementary external polygon extending above the implant shoulder. The sleeve part is mainly designed as an upwardly directed external polygon segment. At the very bottom, the screw has an externally threaded portion intended to engage in the internally threaded bore provided in the implant. The screw has a continuation protruding above the sleeve part with a non-rotationally symmetrical contour for attachment of a screwing-in instrument, so that the rotating screwing-in movement can be transmitted via the adapter connected to the implant. In order to remove the adapter from the implant head, the externally threaded portion of the screw must be unscrewed from the internally threaded bore in the implant. This construction can therefore only be used in implants with an internal thread and with an external polygon protruding above the implant shoulder. Moreover, the fact that the adapter has to be unscrewed from the implant complicates the surgical procedure.

An adapter of the same generic type is described in WO 98/55039. Once again, a sleeve part and a rotatable screw protruding through the sleeve part are provided. At the bottom, facing toward the implant shoulder, the sleeve part has a mating shoulder for receiving the complementary implant shoulder and for frictional engagement with the latter. Above the shoulder portion, the sleeve part is designed as an external polygon segment. At the very bottom, the screw has an externally threaded portion for engagement in the internally threaded bore provided in the implant. The screw has a continuation extending above the sleeve part with an external polygon for attachment of a screwing-in instrument. The torque applied with the attached screwing-in instrument for screwing the implant into the patient's bone is largely transmitted via the frictional connection between the mating shoulder in the sleeve part of the adapter and the implant shoulder. To release the adapter from the implant head, the external polygon segment on the sleeve part must be gripped with a wrench and at the same time, using the screwing-in instrument now rotating in the opposite direction, the externally threaded portion of the screw must be disengaged from the internal thread in the implant head. In the case of dental implants, in the confined space of a patient's mouth with neighboring teeth provided, these work steps with two instruments require great dexterity on the part of the operating surgeon and are always difficult and time-consuming. In the case of alternating positions of the fitted implants, in particular in the upper jaw and lower jaw, it may be difficult to immediately identify the direction of rotation for release when removing the adapter. Finally, this construction of an adapter can likewise be used only for implants with an internal thread.

The ampoule described in WO 98/55039 and used for transporting, storing and making ready an implant directly before insertion into the bone has proven extremely advantageous. For this reason, this ampoule can also be used in connection with the present invention. The ampoule has an outer jacket and can be fitted into an outer capsule. A fixing portion in the ampoule is used for suspending the adapter which is connected coaxially to the implant and holds it in this way. The implant mounted in the ampoule can be removed without touching it, by using an instrument attached to the adapter, through a large lateral cutout in the jacket.

A further problem lies in the recording of the geometric contour, as impression-taking, in the environment of the implant fitted in the patient. In dental implantation technology, the impression taken is used for transfer to a master model on which the appropriate superstructure is produced and which is placed on the inserted implant. Very high precision is demanded here for known reasons.

EP 0 879 024 B1 describes an impression cap for transferring an end, protruding from the human tissue structure, of an implant fitted in the human body, including possible superstructures, to a master model. The outwardly directed implant end has on its outside an undercut contour, while the impression cap has a geometry complementing the undercut contour and engaging therein. This is a snap-in element in the form of a circular lip or individual gripping members. The undercut contour is formed, for example, by an implant geometry tapering in a trumpet shape toward the implant bed. The trumpet-shaped implant end has, adjacent to the area of greatest diameter, an angled, i.e. conical, implant shoulder on which the cap shoulder provided on the impression cap bears. Compared to the previously known prior art, this impression cap permitted a significant simplification of the method of taking an impression and producing the master model. At the same time, it permitted a further improvement in precision. However, one problem is the exact fit of the impression cap in confined positions such as arise, for example, in the patient's mouth in the case of dental implants, with gum projecting onto the implant shoulder and blood being released during the operation.

OBJECT OF THE INVENTION

In view of the above mentioned disadvantages of the adapters known hitherto for gripping and holding implants and for impression-taking, the invention is based on the problem of making available an arrangement perfected for these purposes. In this respect, it is expedient to continue using the advantages of the principle of an impression cap which can be locked on the implant shoulder, as in EP 0 879 024 B1. The arrangement is intended to permit an implant connected to the adapter to be stored in a container under sterile conditions so that a screwing-in instrument can be applied to the adapter for the purpose of removing the arrangement from the container. The ampoule following the structural principle as disclosed in WO 98/55039 can be used as container, and an alternatively usable container with further advantageous production and application characteristics is proposed.

The adapter should be able to be produced inexpensively and be easy to use in a variety of ways. The connection of the adapter to the implant must guarantee a secure hold, i.e. in the preparatory phase of the surgical operation, and, during the operation, the implants intended to be fitted must at all times be able to be safely guided and ought in no case to come loose inadvertently, and the sterility requirements must be satisfied. The adapter ought to substantially simplify the removal of the implant from the container, using the attached screwing-in instrument, and the insertion of the implant into the bone. Finally, however, it must be possible to again release the adapter from the implant without difficulty.

OVERVIEW OF THE INVENTION

The arrangement for handling an implant to be inserted into bone consists of a transfer cap which can be fitted in a releasable manner onto the implant, and of an adapter engaging on the implant. The implant has an implant head and a root portion extending from the implant head. The implant head has an internally located, non-rotationally symmetrical inner contour or, alternatively, one such external contour, an outer implant shoulder, and a shoulder edge located underneath the implant shoulder. Underneath the shoulder edge, the implant has an undercut. The transfer cap has a contact surface complementary to the implant shoulder, and an elastic lip gripping under the shoulder edge and engaging in the undercut. The adapter has a driving section which is intended to engage with a form fit in the inner contour or outer contour on the implant. The adapter also has a plug-type extension which is intended for attachment of an instrument. The transfer cap is provided with an axial passage through which the adapter extends to the implant. When the transfer cap is fitted on the implant and the adapter is plugged in, the driving section of the latter comes into engagement on the inner contour or on the alternatively present outer contour. The adapter lies in the axial passage, and the plug-type extension of the adapter protrudes from the transfer cap.

The following features represent advantageous embodiments of the invention.

The adapter, passing through the axial passage, and the transfer cap are connected to one another in a releasable manner. The release force for severing the connection between implant and transfer cap is greater than the release force for severing the connection between transfer cap and adapter. For the releasable connection between transfer cap and adapter, the transfer cap has an inner portion and the adapter has a holding section which engage with one another in a frictional connection. Alternatively, the transfer cap has an elastically deformable contour and the adapter has a mating contour complementary to the latter, and these engage with one another in a force-fit connection. Finally, the inner portion and the holding section for the frictional connection and the contour and the mating contour for the force-fit connection can be jointly present. The inner portion on the transfer cap is a cylindrical inner wall. The holding section on the adapter is a cylinder portion. The deformable contour on the transfer cap is a bead which narrows the axial passage. The mating contour on the adapter is a radial groove into which the bead locks.

The transfer cap is made in one piece and consists of a pot-shaped hollow body and of a retention wing arranged on the latter. The axial passage opens out at one end on the underside of the hollow body and at the other end on the top side of the retention wing. The elastic lip narrows the axial passage and is provided at the very bottom of the hollow body. The hollow body has the inner contact surface configured as a cone portion fitting onto the implant shoulder. A groove for detaching the retention wing is provided between hollow body and retention wing, the latter extending substantially horizontally, that is to say perpendicular to the axial passage. On the top face of the retention wing, the opening-out axial passage is surrounded by a collar on which an inwardly turned bead is formed. The latter can be provided with indents to increase the elasticity of the collar.

The non-rotationally symmetrical inner contour in the implant is an internal polygon, e.g. an octagon, or the alternatively provided outer contour on the implant is an external polygon, e.g. an octagon. In the case where an inner contour is present in the implant, the driving section on the adapter is an external polygon, e.g. an octagon, or, in the case where an outer contour is alternatively present on the implant, the driving section on the adapter is an internal polygon, e.g. an octagon. The plug-type extension on the adapter is an external polygon. On the adapter, the holding section adjoins the driving section. An intermediate section lies between holding section and plug-type extension, which intermediate section has a first flange and a second flange between which a portion of reduced diameter lies. The first flange has the radial groove, and between the plug-type extension and the second flange there is an annular groove for receiving a retaining ring.

The implant underneath the shoulder edge narrows in a trumpet shape toward the root portion, by which means an undercut is formed. The implant shoulder has an inclination in the region of 30°. The root portion is provided with an external thread, preferably self-cutting. In the case where an inner contour is present on the implant, or in the case where alternatively an outer contour is provided on the implant, an internally threaded portion can be arranged within a blind hole.

The combination of implant, of transfer cap fitted onto the implant, and of adapter extending through the transfer cap, is arranged for operative application in a sterile container, releasable from a fixed position. The plug-type extension for gripping by means of an instrument, in most cases a screwing-in instrument, is positioned accessibly, if appropriate with a coupling part already connected to the plug-type extension. The container for the combination is an ampoule which can be fitted into an outer capsule and which has an outer jacket, a large lateral cutout in the jacket through which the implant mounted in the ampoule can be removed, and a holding portion with a laterally open indent which points in the same direction as the cutout. The adapter carrying the transfer cap and the implant is locked releasably with its intermediate section in the indent, by which means the implant carried by the adapter is mounted contact-free in the ampoule.

The container for the combination can alternatively be a blister pack with a thermoformed bottom mold which has a multi-part depression extending over the outer contour of the arrangement. The depression includes an instrument recess for the plug-type extension, projecting into there, of the adapter, and an implant recess which lies opposite the instrument recess and into which the implant with the fitted transfer cap protrudes.

Between the instrument recess and the implant recess, there are two transverse and mutually aligned guide slits for lightly clamping the retention wing of the transfer cap, by which means the implant supported by the transfer cap is mounted contact-free in the bottom mold. The bottom mold is covered over with a covering, and within the bottom mold it is possible to provide further depressions, e.g. for accommodating an insertion screw.

On removing an impression mold from the implant, after an impression has been taken, the transfer cap detaches and remains in the impression mold. A manipulation implant with an analogous shoulder edge and undercut can be plugged into the impression cap remaining in the impression mold. Upon separation of the impression filled with modeling compound, a master model is obtained with manipulation implant embedded therein. The transfer cap, preferably made of a plastic that can be burned out, again remains in the impression mold.

By virtue of the arrangement according to the invention, proceedings when inserting the implants and when taking an impression are simplified. The number of instruments required is reduced; it is not necessary to have a sleeve on the adapter with the external polygon as locking nut, as a result of which the hitherto required instrument—a holding wrench—is no longer necessary. Thus, it is possible to dispense in particular with the difficult work step of unlocking between adapter and implant after insertion of the implant into the patient's body. Because the impression cap is already seated on the implant at the time of implantation, this sometimes problematic work step is also omitted. In this way, the load applied to the inserted implant is decreased overall in two respects, since it is no longer necessary either to unlock the adapter or to attach the impression cap, which is sometimes very awkward at positions where access is difficult. As a result, the construction of the adapter is less complex, the number of instruments hitherto required is reduced, and the proceedings for implantation and impression-taking are greatly simplified. The load on the newly inserted implant is considerably reduced. Finally, there are all the advantages of using it in combination with the previously tried and tested ampoule. The blister pack proposed as an alternative container further improves the efficiency of the packaging of the arrangement.

BRIEF DESCRIPTION OF THE ATTACHED DRAWINGS

Figure 1B:
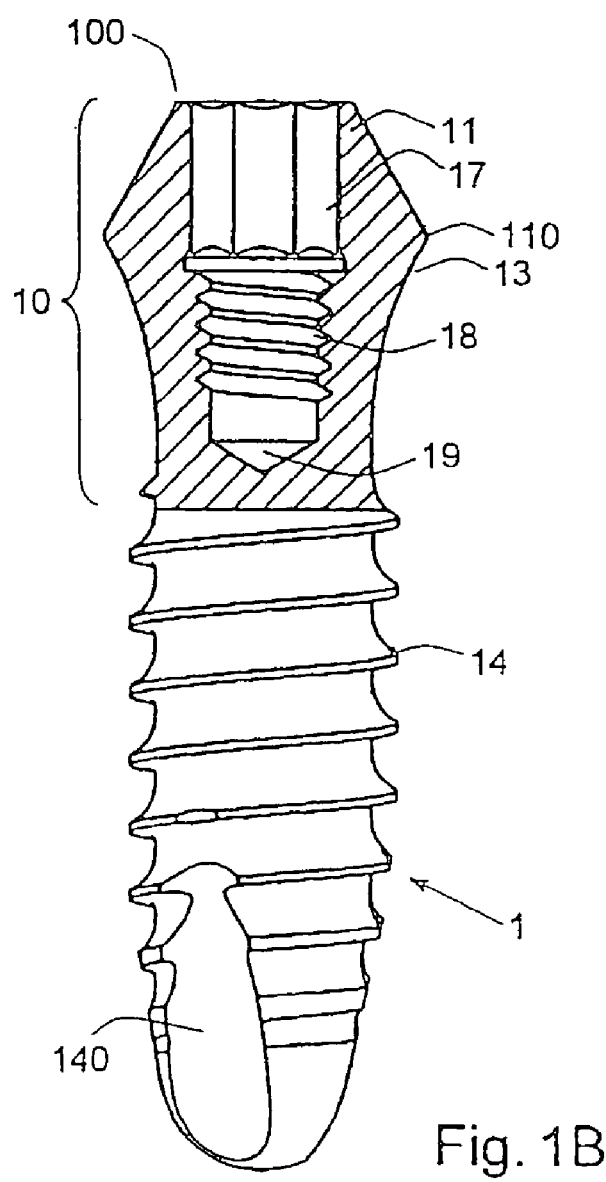
Figure 2A:
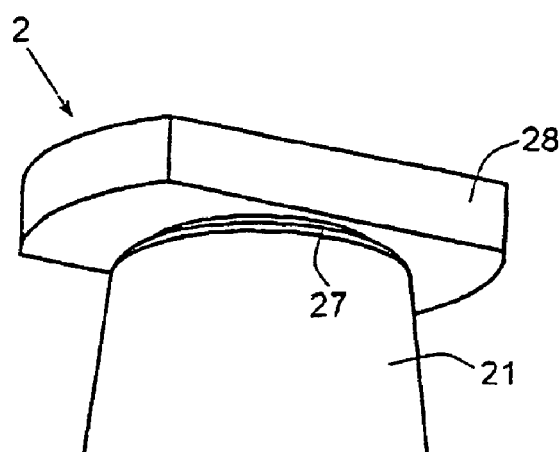
Figure 2B:
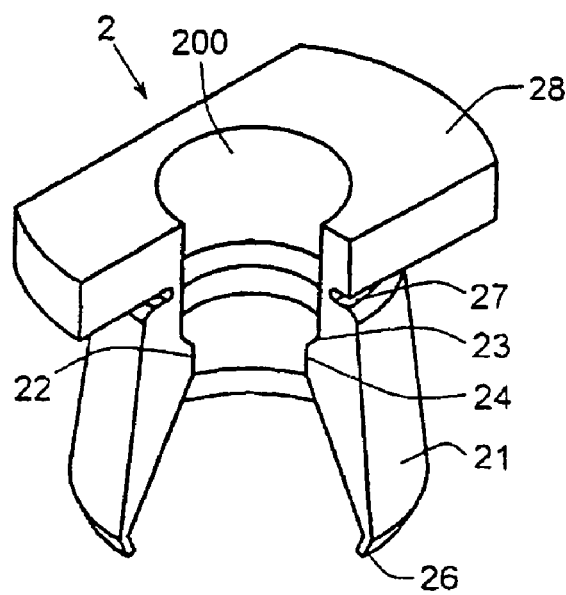
Figure 2C:
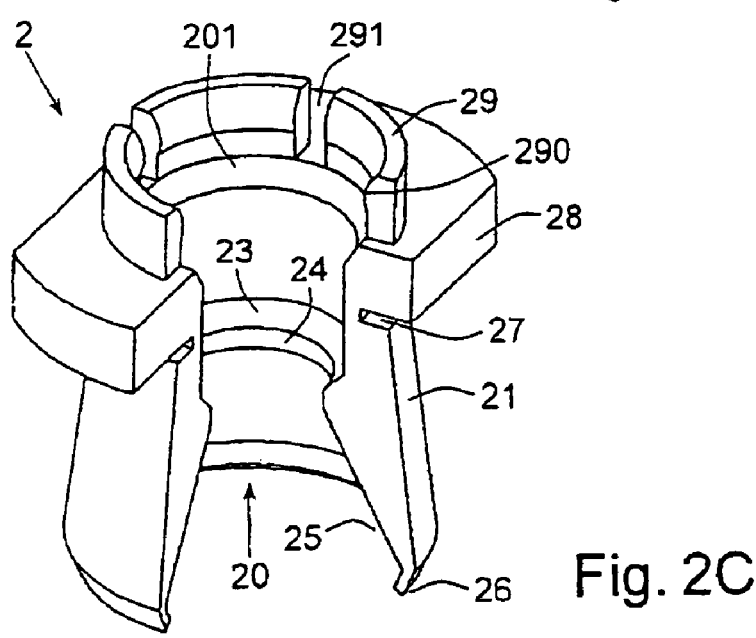
Figure 4A:
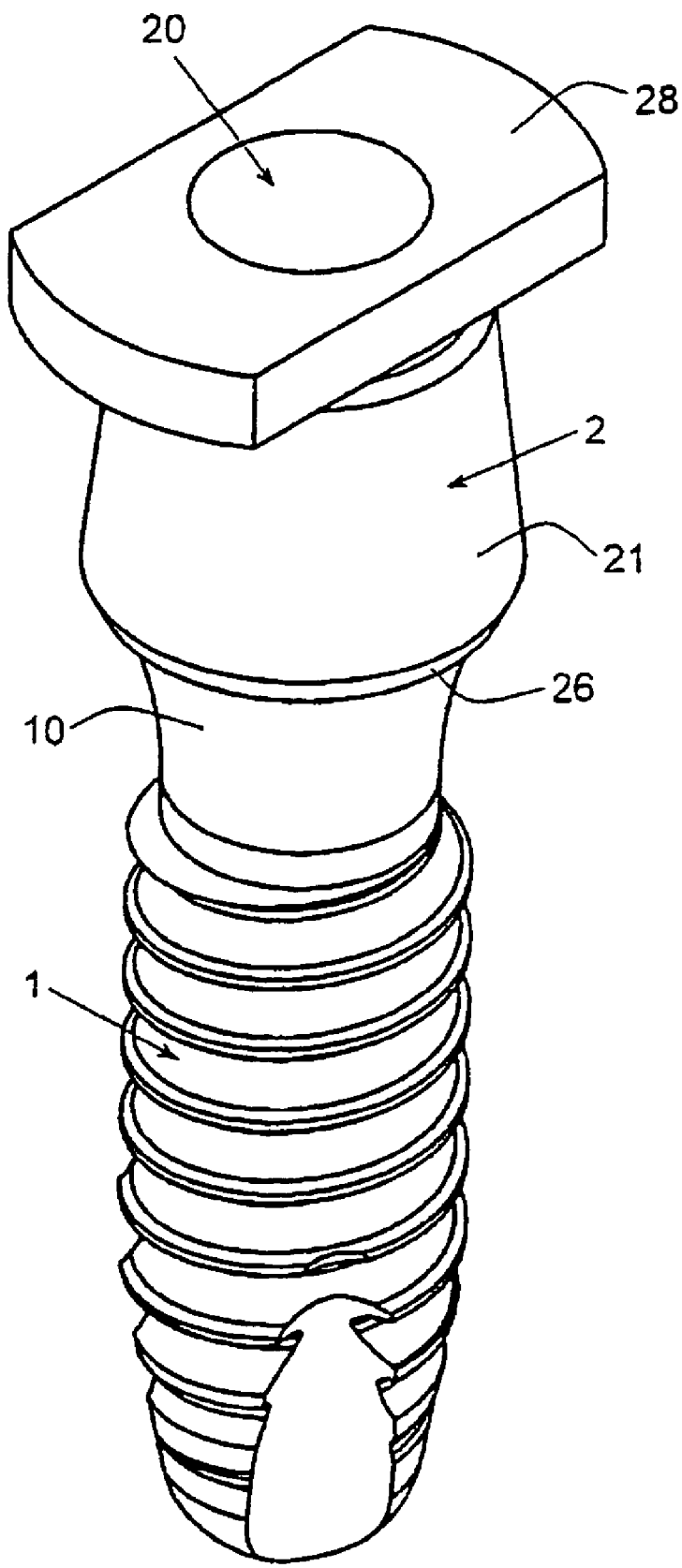
Figure 4B:
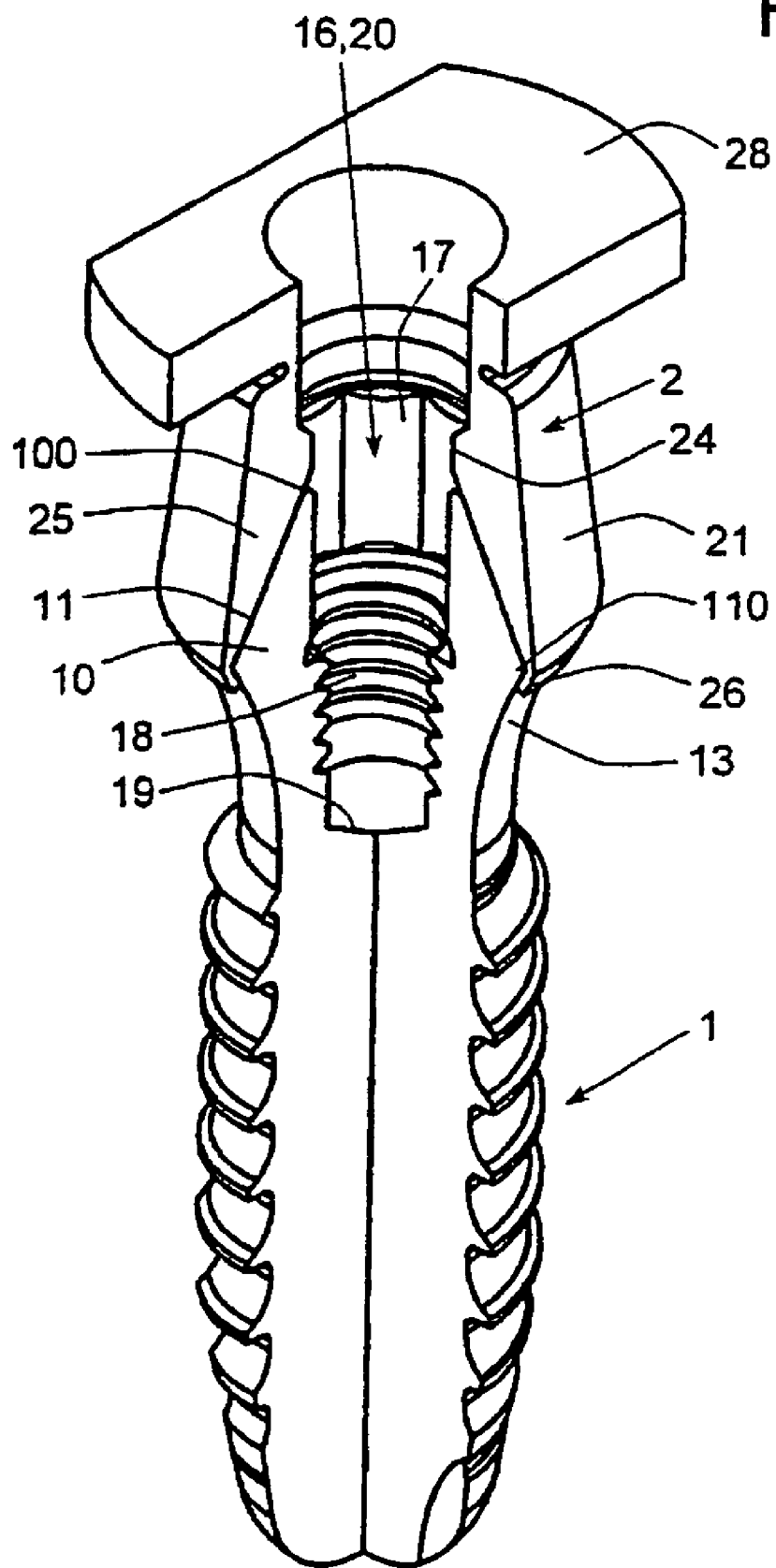
Figure 5A:
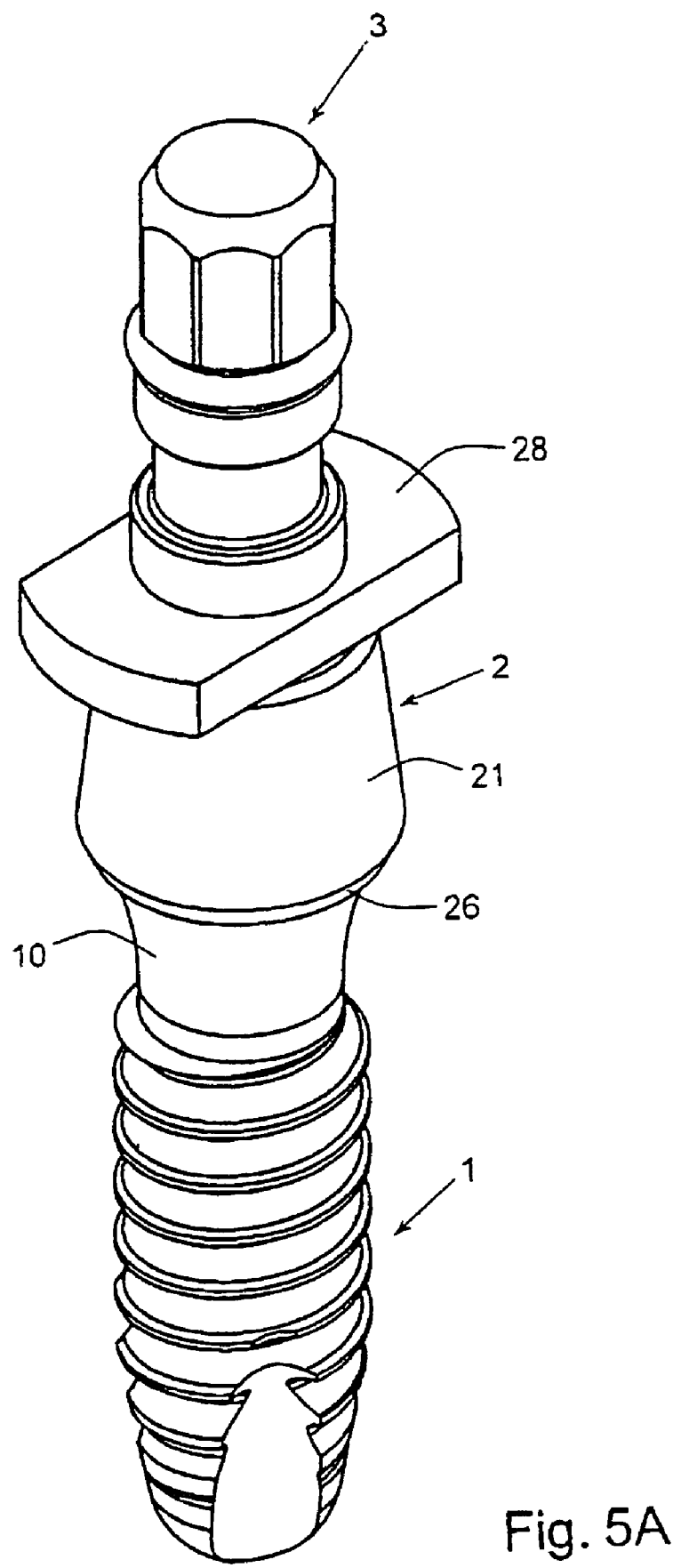
Figure 7A:
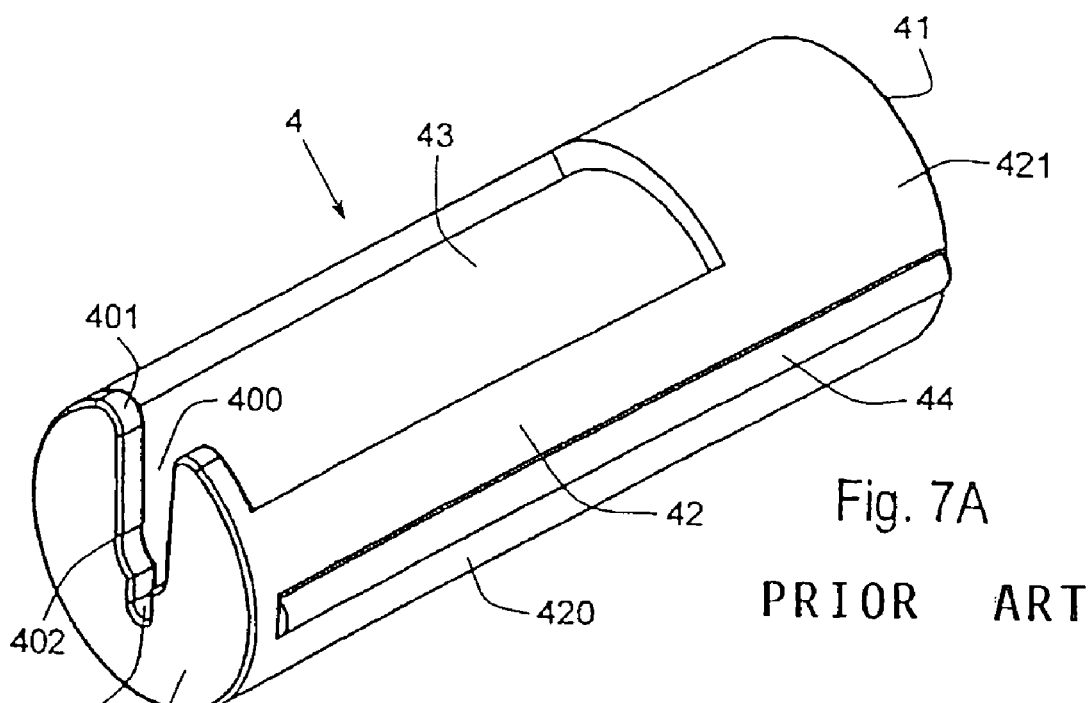
Figure 7B:
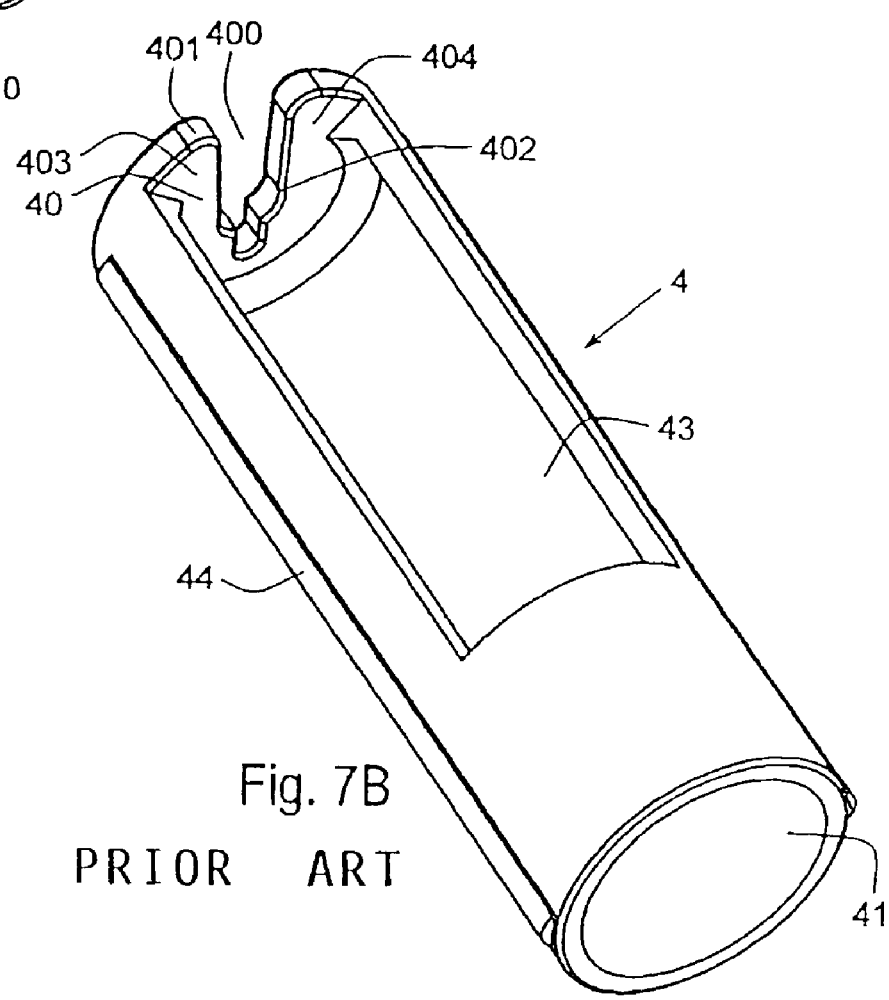
Figure 8B:
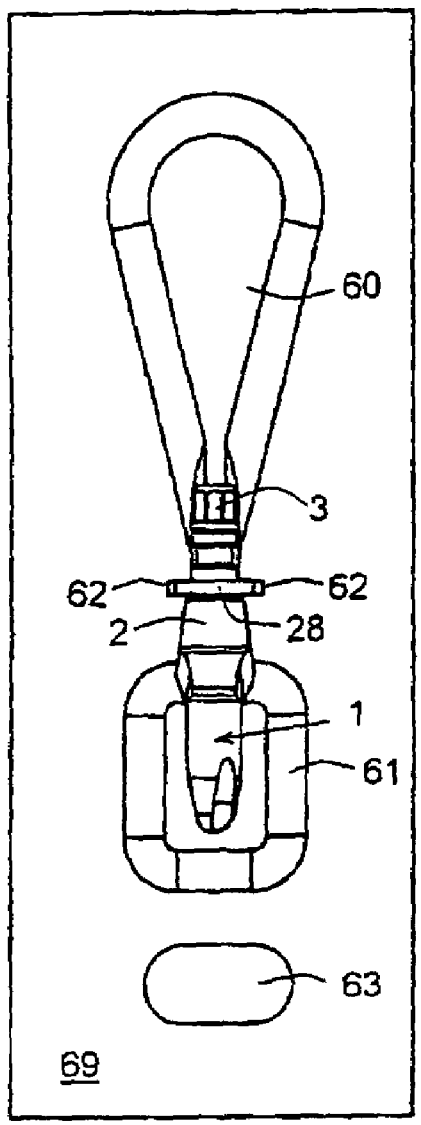
Figure 8C:
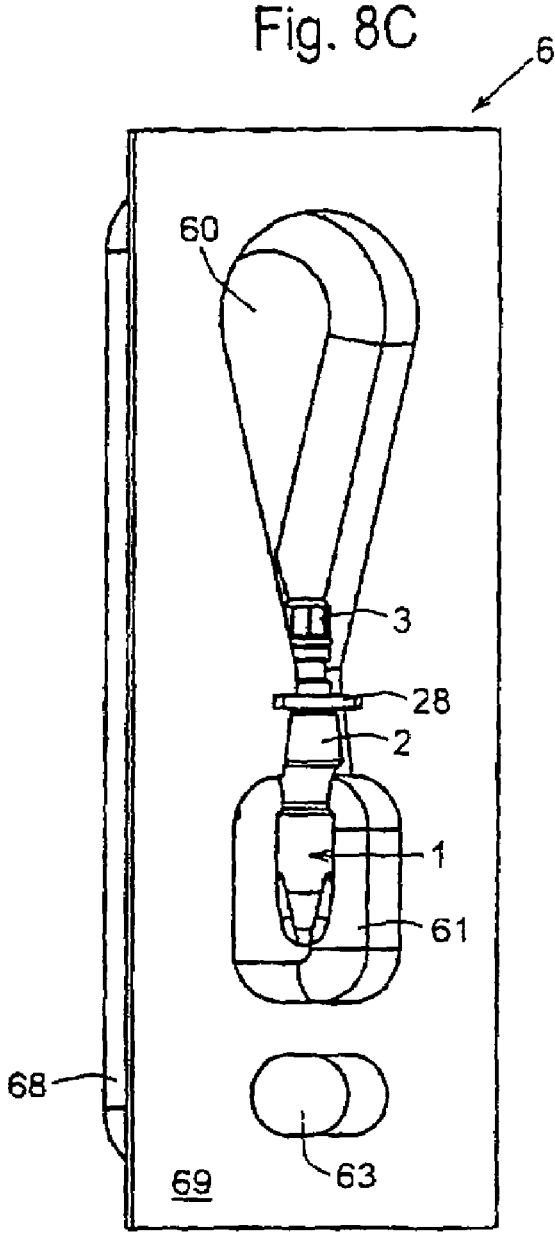
Figure 9B:
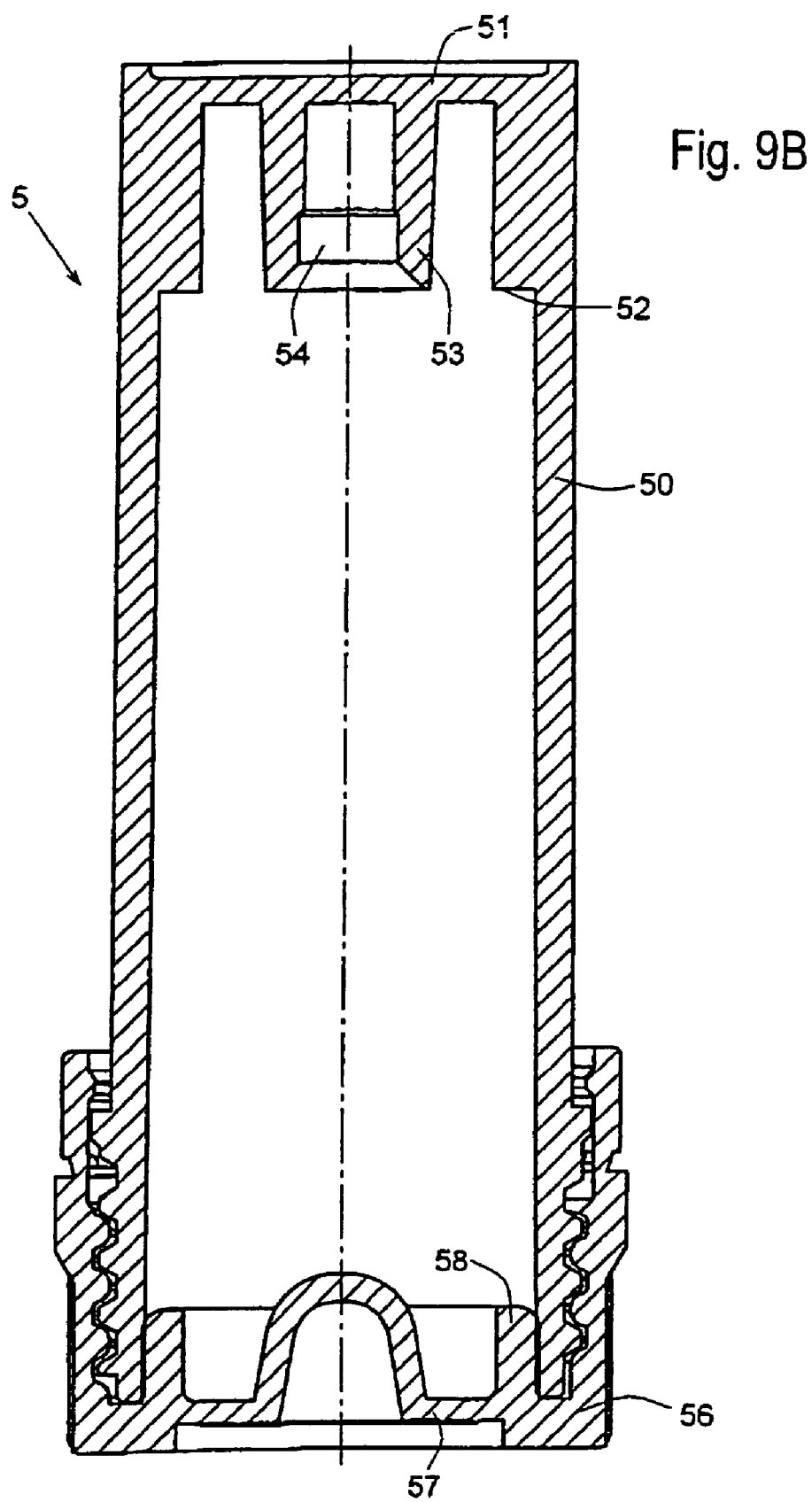
Figure 10B:
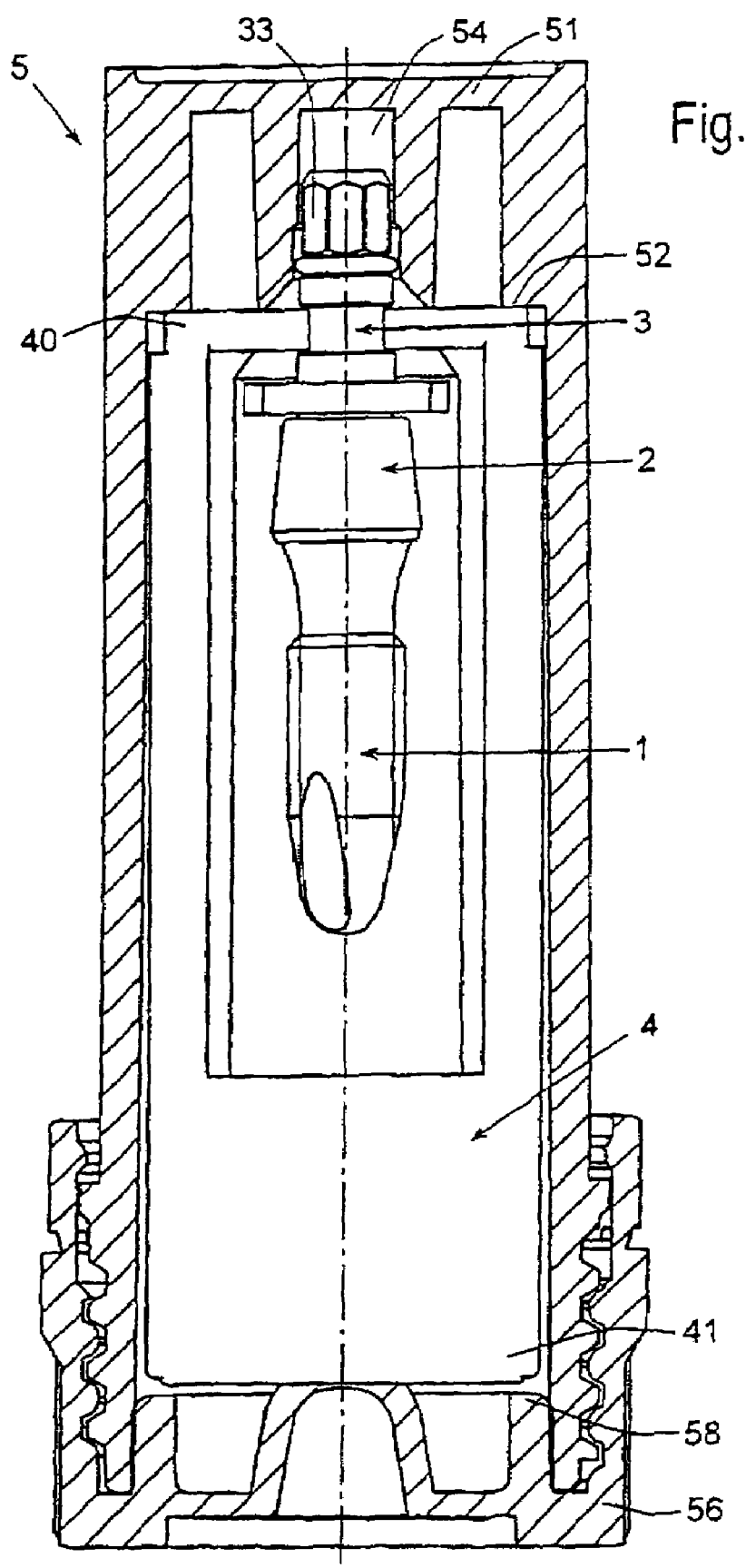
Figure 11D:
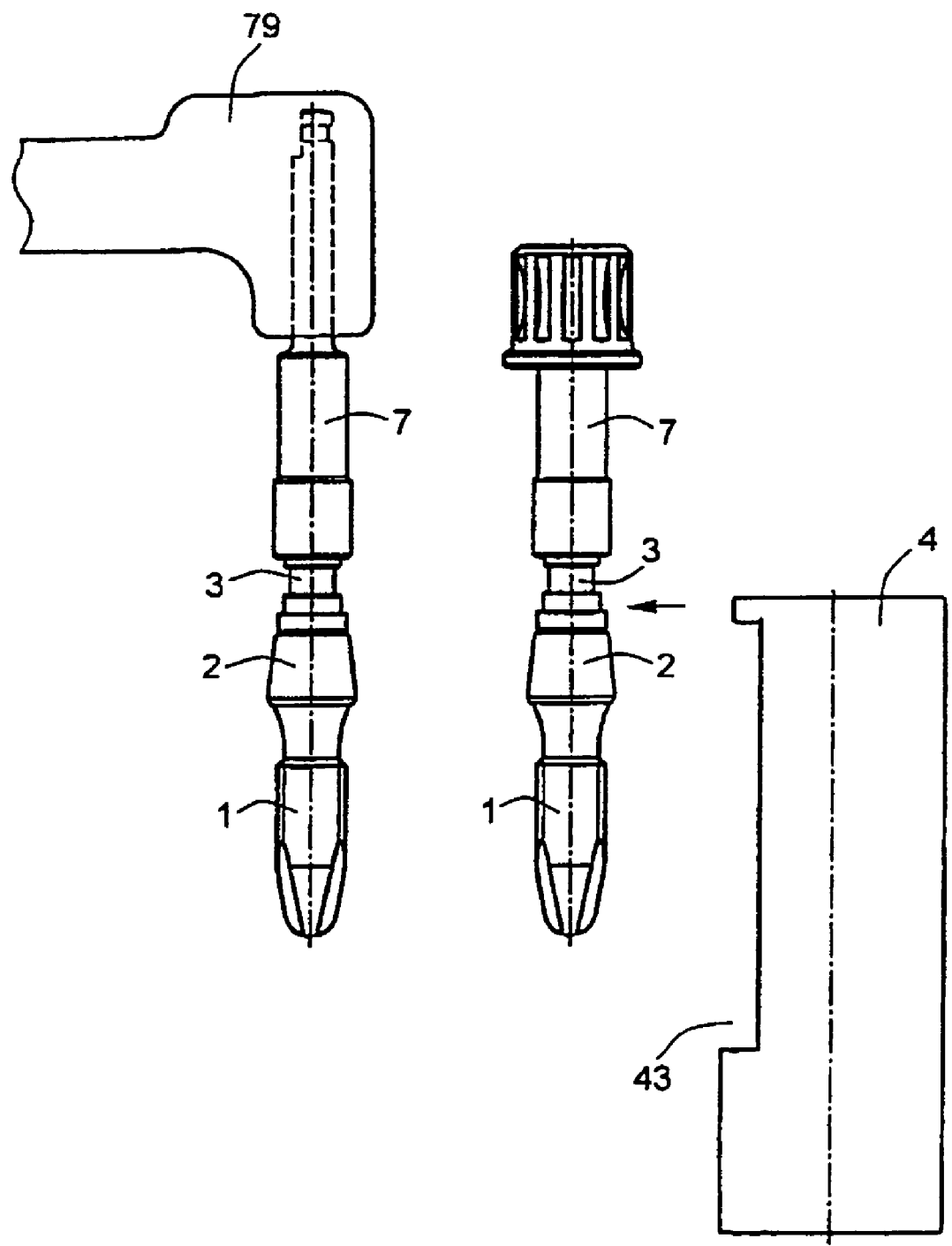
Figure 12F:
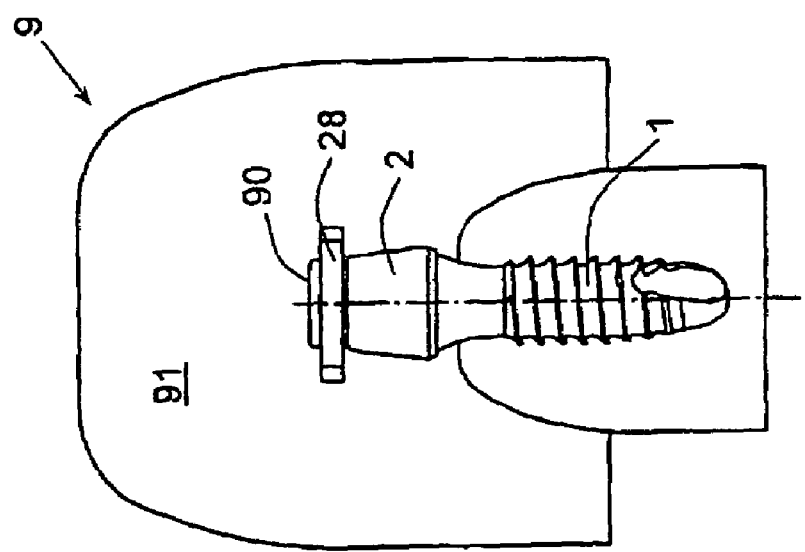
Figure 12E:
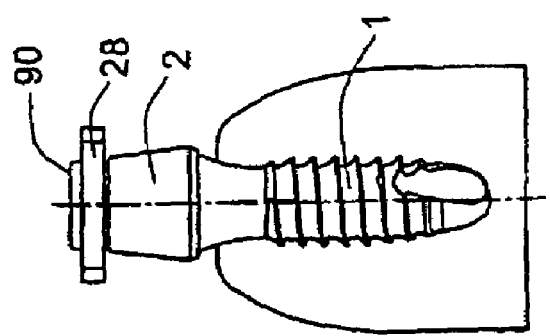
Figure 12D:
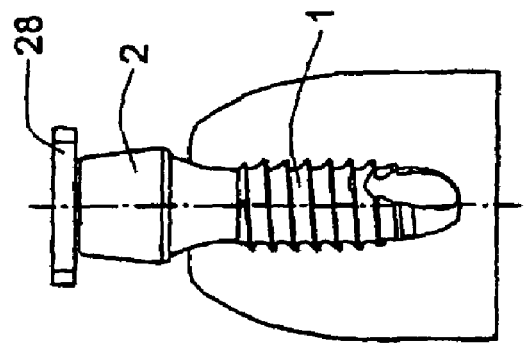
Figure 12H:
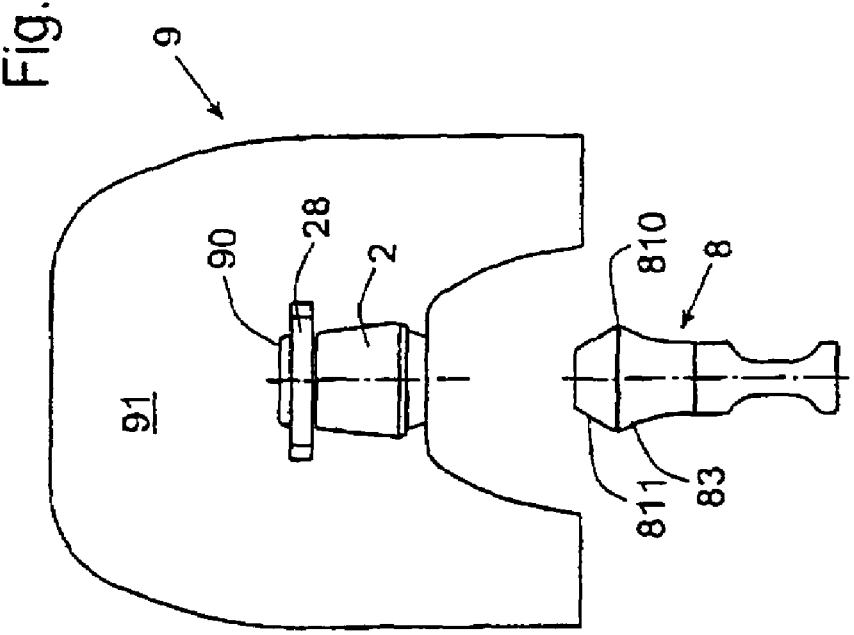
Figure 12G:
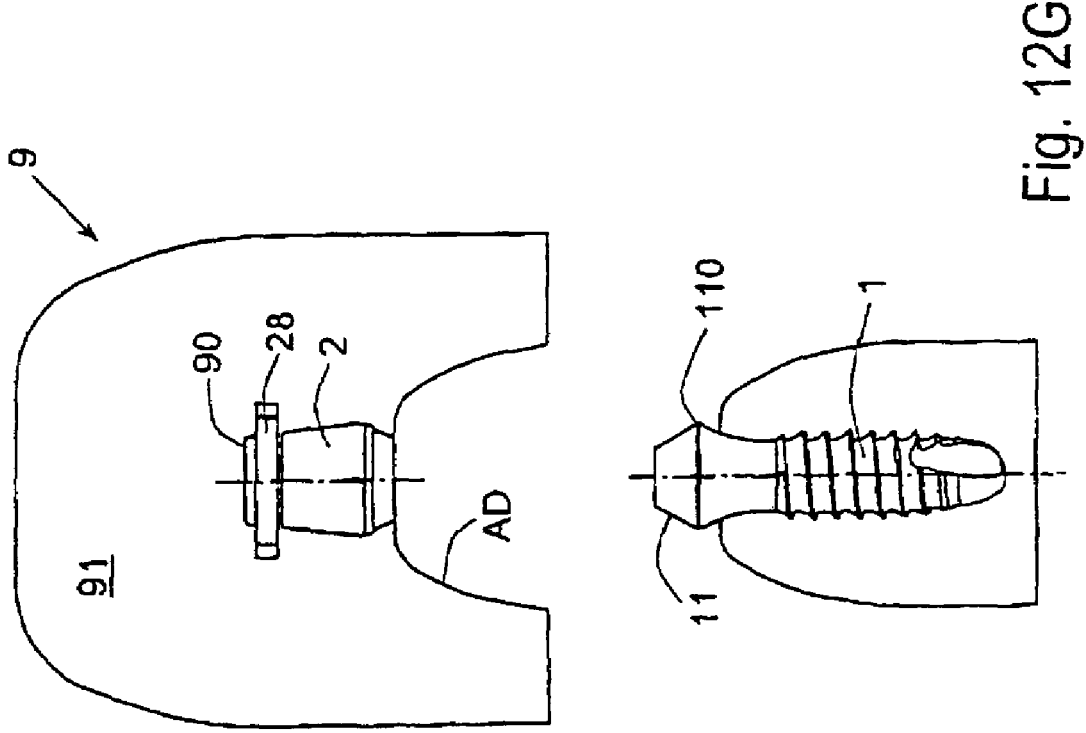

An illustrative embodiment of the arrangement according to the invention is described in detail below with reference to the attached drawings. For the sake of completeness, the already known ampoule for storing the implant is also described insofar as is necessary for explaining the invention. Possible modifications are mentioned at the end of the description. In the drawings:

FIG. 1A: shows a perspective view of a largely known implant in the form of a solid screw;

FIG. 1B: shows the implant according to FIG. 1A in partial cross section;

FIG. 2A: shows a perspective view of a transfer cap according to the invention;

FIG. 2B: shows the transfer cap according to FIG. 2A in another perspective, and in partial cross section;

FIG. 2C: shows the illustration according to FIG. 2B with a collar over the retention wing;

FIG. 3A: shows a perspective view of an adapter according to the invention;

FIG. 3B: shows the adapter according to FIG. 3A with an O-ring attached;

FIG. 3C: shows the adapter according to FIG. 3A, in another perspective, with an additional locking groove for engagement of the locking elements of the collar of the transfer cap according to FIG. 2C;

FIG. 4A: shows a perspective view of the implant according to FIG. 1A with attached transfer cap according to FIG. 2A;

FIG. 4B: shows the illustration according to FIG. 4A in partial cross section;

FIG. 5A: shows a perspective view of the combination of implant and transfer cap according to FIG. 4A with fitted adapter according to FIG. 3A;

FIG. 5B: shows the illustration according to FIG. 5A in partial cross section;

FIG. 5C: shows, in partial cross section, the combination according to FIG. 5A, in another and smaller perspective, with the modified transfer cap according to FIG. 2C;

FIG. 6A: shows a combination of an implant with an external polygon, a modified transfer cap, with an inserted, modified adapter, in partial cross section and in perspective;

FIG. 6B: shows the combination according to FIG. 6A partially in vertical cross section;

FIG. 7A: shows an ampoule known per se, in a perspective view looking toward the outside of the fixing portion;

FIG. 7B: shows the ampoule according to FIG. 7A in a perspective view looking toward the inside of the fixing portion;

FIG. 7C: shows a front view of the ampoule according to FIG. 7A, in partial cross section;

FIG. 7D: shows the ampoule according to FIG. 7A in a plan view looking toward the outside of the fixing portion;

FIG. 7E: shows a front view of the combination of implant according to FIG. 1A, transfer cap according to FIG. 2A, and adapter according to FIG. 3B, fitted into the ampoule according to FIG. 7A;

FIG. 8A: shows a perspective plan view of a blister pack as an alternative container for storing the combination of implant according to FIG. 1A, transfer cap according to FIG. 2A, and adapter according to FIG. 3A;

FIG. 8B: shows a plan view of the blister pack according to FIG. 8A, with inserted combination of implant according to FIG. 1A, transfer cap according to FIG. 2A, and adapter according to FIG. 3B;

FIG. 8C: shows the illustration according to FIG. 8B in a perspective plan view;

FIG. 8D: shows the illustration according to FIG. 8B, with attached coupling piece;

FIG. 8E: shows the illustration according to FIG. 8D in a perspective plan view;

FIG. 9A: shows a perspective view of an outer capsule known per se, with lid unscrewed;

FIG. 9B: shows the outer capsule according to FIG. 9A with screwed-on lid, in vertical cross section;

FIG. 10A: shows, in partial cross section, the combination, according to FIG. 7E, of implant, transfer cap and adapter fitted into the ampoule and surrounded by an outer capsule according to FIG. 9A, with lid unscrewed;

FIG. 10B: shows, in partial cross section, the illustration according to FIG. 10A, with ampoule fitted in a closed outer capsule, during storage or transport and in the starting situation for operative handling;

FIGS. 11A through 12M: show the principle operative handling of the arrangement, beginning in the starting situation according to FIG. 10B and ending with production of the master model and subsequent steps;

FIG. 11A: step 1—opening the outer capsule by unscrewing the lid, and emptying the ampoule from the outer capsule;

FIG. 11B: step 2—making ready the respective coupling pieces for the alternative screwing-in instruments for attachment to the adapter;

FIG. 11C: step 3—attaching a ratchet coupling to the adapter;

FIG. 11D: step 4—removing the implant from the ampoule, with alternatively a ratchet coupling attached to the adapter or with a coupling piece for motorized drive;

FIG. 12A: step 5—ratchet coupling attached to the adapter, and implant screwed into the bone;

FIG. 12B: step 6—screwing the implant into the bone until the intended depth is reached;

FIG. 12C: step 7—removing the ratchet coupling from the adapter upon completion of the screwing-in of the implant;

FIG. 12D: step 8—withdrawing the adapter from the fitted implant, with the transfer cap remaining locked on said implant;

FIG. 12E: step 9—closing the access opening into the transfer cap;

FIG. 12F: step 10—placing the impression tray, filled with impression compound, onto the fitted implant with the locked-on transfer cap, in order to take an impression;

FIG. 12G: step 11—removing the impression tray from the fitted implant, the transfer cap remains in the impression tray, the impression is taken;

FIG. 12H: step 12—advancing a manipulating implant toward the transfer cap remaining in the impression tray;

FIG. 12I: step 13—inserting the manipulating implant into the transfer cap remaining in the impression tray;

FIG. 12J: step 14—filling the impression, in which the manipulating implant sits, with impression compound;

FIG. 12K: step 15—removing the impression tray from the master model obtained, the transfer cap remains in the impression tray, the manipulating implant remains in the master model;

FIG. 12L: step 16—removing the transfer cap from the impression tray and placing it on the manipulating implant sitting in the master model;

FIG. 12M: step 17—detaching the retention wing from the transfer cap sitting on the manipulating implant;

FIGS. 13A through 13G: show, in a shortened sequence, the principle of the operative handling with the modified arrangement according to FIG. 6A, starting at an already advanced stage, with completed step 4, and up to the production of the master model;

FIG. 13A: step 4—the implant was removed from a container (not shown) either with a ratchet coupling attached to the adapter or with a coupling piece for motorized drive;

FIG. 13B: step 5—ratchet coupling attached to the adapter, and implant screwed into the bone;

FIG. 13C: step 7—removing the ratchet coupling from the adapter upon completion of the screwing-in of the implant; with screwing the implant into the bone until the intended depth is reached, step 6 was already performed;

FIG. 13D: step 10—placing the impression tray, filled with impression compound, onto the fitted implant with the locked-on transfer cap, and the adapter sitting therein, in order to take an impression; previous steps 8 and 9 involving withdrawal of the adapter and closure of the access opening into the transfer cap are omitted here;

FIG. 13E: step 11—removing the impression tray from the fitted implant; the transfer cap and adapter remain in the impression tray, the impression is taken;

FIG. 13F: step 13—inserting the modified manipulating implant into the transfer cap remaining in the impression tray; by advancing a manipulating implant toward the transfer cap remaining in the impression tray, step 12 has already been performed;

FIG. 13G: step 15—removing the impression tray from the master model obtained, the transfer cap remains in the impression tray, the manipulating implant remains in the master model; by filling the impression, in which the modified manipulating implant sits, with impression compound, step 14 has already been performed.

ILLUSTRATIVE EMBODIMENTS

The following observation applies to the whole of the description below. If reference numbers are indicated in a figure for the purposes of clarity of the drawings but are not mentioned in the directly relevant part of the description, then reference is made to where these were mentioned in the descriptions of previous figures. For the sake of clarity, repeated mention of structural parts appearing in successive figures is for the most part avoided, as long as the drawings clearly show that these are "recurring" structural parts.

FIGS. 1A and 1B

The implant 1 is here in the form of a solid screw and has an elongate body, with the implant head 10 which is located at the top, ends at its very top with the in principle annular crest 100, and lies in the horizontal plane. The implant shoulder 11 widening conically in the apical direction extends from the crest 100 and ends at the shoulder edge 110 which has the maximum diameter on the implant head 10. The implant shoulder 11 is at an angle of, for example, 30° to the perpendicular and can be made relatively wide compared to customary dimensions. Underneath the shoulder edge 110, the implant head 10 narrows in a trumpet shape and merges into the root portion 12, so that an undercut 13 is obtained under the shoulder edge 110. The apically extending root portion 12 has the external thread 14, ends at the implant tip 15, and is intended for insertion into the bone. The external thread 14 is preferably self-cutting and has cutting edges 140 in the area of the implant tip 15. A blind hole 16 extending axially into the implant 1, by the height of the implant head 10, opens out within the crest 100. Provided in the blind hole 16 there is a non-rotationally symmetrical inner contour 17, for example an internal octagon, which reaches approximately as far as the level of the shoulder edge 110. Lying underneath the inner contour 17 there is an internally threaded portion 18 which extends as far as the base 19 of the bore. As will be described later, the inner contour 17 is used to receive an adapter. The internally threaded portion 18 can be used to receive an insertion screw or for screwing-in the prosthesis, for example in the form of a bar or bridge. Generally, the implant 1 is made in most cases of titanium and, on the outside, has a special surface structure which promotes osseointegration.

FIGS. 2A and 2B

The one-piece transfer cap 2 consists principally of a pot-shaped hollow body 21 and of a plate-like retention wing 28 which horizontally covers the top of the hollow body 21. Hollow body 21 and retention wing 28 are connected to one another at a separating site with an external radially extending groove 27 and resulting reduced wall thickness. Extending through the transfer cap 2 there is an axial passage 20 which, as cylinder portion 200, opens out on the top face of the retention wing 28 and reaches to below the level of the groove 27. Adjoining the cylinder portion 200 there is a ledge 22 of trapezoidal cross section which narrows the clearance width of the axial passage 20. On the top of the ledge 22 there is an annular seat surface 23 which widens conically toward the cylinder portion 200. With respect to the axis of the axial passage 20, the ledge 22 has a perpendicular annular face 24 from which a cone portion 25 extends, widening toward the underside of the hollow body 21. At the very bottom the hollow body 21 has a circularly extending, elastic lip 26 which, turned inward, once again narrows the end of the axial passage 20 widening toward the site of the lip 26. From the groove 27 to the lower mouth of the axial passage 20, the hollow body 21 widens conically on the outside so that the greatest wall thickness is present in the area of the ledge 22, this wall thickness decreasing toward the site of the lip 26.

FIG. 2C

In a modification of the transfer cap 2, the mouth of the axial passage 20 on the top face of the retention wing 28 is provided with an outwardly opening bevel 201, and this mouth is surrounded by a collar 29. An inwardly directed bead 290 is formed on the collar 29. Indentations 291 contribute to increasing the elasticity of the collar 29.

The retention wing 28 which is provided previously on the transfer cap 2, and which adjoins the hollow body 21 above a groove 27 narrowing the wall and has the basic shape of a rectangular rounded plate, could be modified. The groove 27 is dispensable, the wing 28 could be designed as a circular plate with no rotation-securing action, and, finally, the wing 28 can be dispensed with altogether.

FIGS. 3A and 3B

The adapter 3 illustrated is in one piece and has the basic configuration of a bolt provided with many different contours. The structure of the adapter 3 is made up of the driving section 30 forming the lower end, the adjacent holding section 31, the intermediate section 32 lying above the latter, and the plug-type extension 33 forming the upper end. The driving section 30 has a non-rotationally symmetrical outer contour 300, e.g. a complementary octagon, for form-fit insertion into the inner contour 17 on the implant 1. The outer contour 300 runs out as a beveled surface 301 at the transition to the holding section 31. The holding section 31 is formed by a cylindrical portion which starts at the beveled surface 301. Seen from the direction of the holding section 31, the intermediate section 32 consists of a first cylindrical flange 320, a second cylindrical flange 323, and the cylinder portion 322 of reduced diameter lying between the two flanges 320, 323. Above the second flange 323, the plug-type extension 33 begins with an annular groove 331 for receiving a retaining ring 332, preferably in the form of an O-ring. Otherwise, the plug-type extension 33 is provided with a non-rotationally symmetrical outer contour 330, e.g. an octagon, for form-fit attachment of a coupling piece for a screwing-in instrument.

FIG. 3C

In a variation of the adapter 3, for interaction with the modified transfer cap 2 according to FIG. 2C, the holding section 31 extends as far as the first cylindrical flange 320, on which a radial groove 321 is arranged.

FIGS. 4A and 4B

When locked in place, the removable transfer cap 2 sits with its internal cone portion 25 on the implant shoulder 11 and, with its lip 26, it surrounds the shoulder edge 110 so that the lip 26 engages in the undercut 13, which has a reduced diameter in relation to the shoulder edge 110. The blind hole 16 of the implant 1 and the axial passage 20 of the transfer cap 2 are coaxial to one another. The annular face 24 with the least clearance width inside the transfer cap 2 comes to lie above the crest 100 of the implant 1. In doing so, the axial access to the inner contour 17 in the implant 1 for the adapter 3 to be inserted remains fully open (see FIGS. 5A and 5B).

FIGS. 5A and 5B

When the transfer cap 2 is locked onto the implant 1 and the adapter 3 is inserted to its full depth into this combination, the driving section 30 of the adapter 3 engages in the inner contour 17 in the implant 1, and the holding section 31 of the adapter 3 is gripped with defined frictional connection by the cylinder portion 200 of the transfer cap 2. The annular face 24 of the transfer cap 2 surrounds the beveled face 301, and the first cylindrical flange 320 of the intermediate section 32 of the transfer cap 2 sits on the top face of the retention plate 28, at the edge of the axial passage 20 opening out here. The frictional connection between the transfer cap 2 and the adapter 3 is dimensioned so that although the adapter 3 inserted in the transfer cap 2 and in the implant 1 does not inadvertently slide out, said adapter 3 can nevertheless be withdrawn with acceptable loading for an inserted implant 1.

FIG. 5C

In the arrangement comprising the implant 1, the modified transfer cap 2 according to FIG. 2C and the modified adapter 3 according to FIG. 3C, the hold of the adapter 3 in the transfer cap 2 is made even more secure. When the adapter 3 is inserted to its full depth, the bead 290 of the elastically spreadable collar 29 of the transfer cap 2 engages in the radial groove 321 in the first flange 320 of the lengthened holding section 31 on the adapter 3. When withdrawing the adapter 3 from the arrangement, it is necessary to overcome the frictional connection between cylinder portion 200 and holding section 31 and the restraining force by the elastically releasable engagement between bead 290 and radial groove 321.

FIGS. 6A and 6B

In this combination of implant 1, transfer cap 2 and adapter 3, the component parts are modified. The modifications pertain to an implant 1 whose head area 10 has been modified and which, above the implant shoulder 11, has an external polygon 101 with its radially distributed flats 102, e.g. eight in number. In the coronal direction, as far as the crest 100, the flats 102 merge into a tapering cone 103. Otherwise, this implant 1 again has a root portion 12 which extends to the apical implant tip 15 and which has the external thread 14 and the cutting edges 140. On the outside, the implant head 10 once again has the implant shoulder 11 which ends at the shoulder edge 110, below which the undercut 13 lies. The mouth of the blind hole 16, with internal thread 18, extending axially into the implant 1 as far as the bore base 19 is surrounded by the crest 100.

Given the presence of the external polygon 101 on the implant 1, the adapter 3 has changed significantly at its driving section 30, from which there extends, to a point above the holding section 31, as far as the bore base 325, an axial blind hole 34 in which, in the assembled state, the external polygon 101 is placed. The flats 102 are gripped with a form fit by a complementary inner contour 302 on the driving section 30 of the adapter 3. Below the plug-type extension 33, the adapter again has the annular groove 331 adjoined by a cylindrical flange 323 which is followed by a polygonal disk 324 of wider diameter. The holding section 31 extends below the polygonal disk 324 and merges into the driving section 30.

The transfer cap 2 is in principle unchanged. The circular lip 26 runs around the far bottom of the hollow body 21, while in the coronal direction there is the retention wing 28, on which the collar 29 is situated. Large apertures 210 are present in the hollow body 21, and the retention wing 28 has peripheral bores 280 which can serve for application of a securing line. The apertures 210 permit introduction of impression compound 91 at the holding section 31 of the adapter 3, by which means the assembled combination acquires additional fixing. In the assembled state, the transfer cap 2 is locked onto the implant shoulder 11, the lip 26 gripping under the implant shoulder 11 and engaging in the undercut 13. The adapter 3 bears with its polygonal disk 324 on the collar 29 of the transfer cap 2, and the holding section 31 lies with defined static friction in the hollow body 21. The driving section 30 surrounds the raised external polygon 101.

FIGS. 7A through 7D

As a first alternative of a container for storing the arrangement of implant 1, transfer cap 2 and adapter 3, the already known ampoule 4 is described by way of a general example. At the first end face, the ampoule 4 has a holding portion 40 and, on the second end face remote from this, it has a stand portion 41. Extending between holding portion 40 and stand portion 41 is the cylinder jacket 42, with the large cutout 43 which extends from the holding portion 40 to the stand portion 41. The implant 1 held in the ampoule 4 can be removed via the lateral cutout 43. The cylinder jacket 42 remaining in the area of the cutout 43 has the form of an open shell 420, while in the stand portion 41 the cylinder jacket 42 provides a tubular portion 421. The second end face is preferably open.

The holding portion 40 has the form of a circular end plate, so that this end face is substantially closed, and the cylinder jacket 42 lies perpendicular to the holding portion 40. In the holding portion 40 there is a laterally open indent 400 which points in the same direction as the cutout 43. The indent 400 is slit-shaped with rounded parts 401 at the peripheral entrance. Lying in the course of the indent 400 there is a constriction 402, behind which the indent 400 continues in a semicircle shape. This results in the formation of two opposite jaws 403, 404 on the holding portion 40. Beyond the indent 400, cutting further into the holding portion 40 toward the cylinder jacket 42, an expansion groove 405 is provided so that, when an adapter 3 carrying an implant 1 is forced in or forced out, the jaws 403, 404 are better able to spread elastically. After the adapter 3 has been forced in and the constriction 402 has overcome the latter's cross section, the adapter 3 engages in the indent 400, and the jaws 403, 404 close together again. An asymmetrical distribution of material, and beads 44 arranged on the outside of the cylinder jacket 42, have a damping action on a rolling ampoule 4 and prevent it from continuing to roll.

FIG. 7E

The arrangement of implant 1 with locked-on transfer cap 2 and with an adapter 3 inserted into both of them is fitted into the ampoule 4. The implant 1 projects into the inside of the ampoule 4 without touching the latter's cylinder jacket 42 and lies underneath the window-like cutout 43. With the intermediate section 32, the adapter 3 is locked into the indent 400 of the holding portion 40 of the ampoule 4. The cylinder portion 322 lies underneath the constriction 402, and the two adjoining flanges 320, 323 engage on the holding portion 40. The plug-type extension 33 of the adapter 3 protrudes freely outward so that an instrument for gripping the arrangement and withdrawing it from the ampoule 4 can be attached thereto.

FIGS. 8A through 8E

As a second suitable alternative of a container for storing the arrangement of implant 1, transfer cap 2 and adapter 3, a blister pack is proposed with a horizontal plate 69 and a shell part 68 extending downward from the latter. In the thermoformed bottom mold 6 advantageously made of transparent plastic, a depression is provided which extends widely across the outer contour of the arrangement and which is divided into three sections, namely, on the one hand, an instrument recess 60 for the plug-type extension 33 of the adapter 3 protruding into it; on the other hand the depression consists of an implant recess 61 into which the implant 1 with the attached transfer cap 2 extends. Between the instrument recess 60 and the opposite implant recess 61, there are two transversely extending and mutually aligned guide slits 62 for lightly clamping the retention plate 28 of the transfer cap 2.

The depth and size of the recesses 60, 61 and slits 62 are such that, in the instrument recess 60, the free space necessary for attachment of a coupling piece 7 and screwing-in instrument, e.g. a dental handpiece 79, is present. The implant 1 is positioned in the implant recess 61 in such a way that it touches neither the side walls nor the base of the bottom mold 6 and in no event does it come into contact with the cover (not shown) for covering the bottom mold 6. Further depressions 63 can be provided inside the bottom mold 6, e.g. for introduction of an insertion screw.

FIGS. 9A and 9B

In the completed state, the ampoule 4, with the inserted arrangement comprising implant 1, transfer cap 2 and adapter 3, is inserted into an outer capsule 5. The outer capsule 5 consists of a hollow cylinder 50 whose base 51 is closed, and of a screw-on closure lid 56. On the inside, at a distance from the base 51, the edge of the cylinder 50 is provided with a peripheral contact shoulder 52 which serves as an axial abutment for the inserted ampoule 4. Extending from the level of the contact shoulder 52 toward the base 51, and situated centrally in the cylinder 50, there is a funnel seat 53 with a blind hole 54. The interior of the cylinder 50 widens slightly conically toward the opening in order to make it easier to empty out the inserted ampoule 4 and to exclude the possibility of jamming. The closure lid 56 has a base 57 from which a radially extending shoulder 58 extends into the opening of the cylinder 50. The shoulder 58 of the closure lid 56 also constitutes an axial abutment for the inserted ampoule 4.

FIGS. 10A and 10B

With the equipped ampoule 4 inserted into the outer capsule 5, the holding portion 40 of the ampoule 4 is facing toward the base 51 of the outer capsule 5, while the standing portion 41 of the ampoule 4 points in the direction of the closure lid 56 of the outer capsule 5. The plug-type extension 33 of the adapter 3 protrudes into the blind hole 54 located inside the outer capsule 5. With the closure lid 56 screwed on, the ampoule 4 is axially stabilized between the contact shoulder 52 of the cylinder 50 and the shoulder 58 on the closure lid 56.

FIGS. 11A through 11D

The step-by-step handling of the arrangement with implant 1, transfer cap 2 and adapter 3 is explained with reference to the following sequence of figures, taking the example of an ampoule 4 with outer capsule 5 as container, up to the point prior to insertion of the implant 1 into the bone. The example concerns the insertion of a dental implant into the human jaw bone. The starting point is where the arrangement consisting of implant 1, transfer cap 2 and adapter 3 is fitted in an ampoule 4 which in turn is situated in an outer capsule 5. The adapter 3 clamped in the holding portion 40 of the ampoule 4 holds the implant 1 with the locked-on transfer cap 2 in position. The entire content of the outer capsule 5 is sterile.

FIG. 11A→step 1: To open the outer capsule 5, the closure lid 56 has been removed from the cylinder 50. The ampoule 4 with the arrangement contained in it is tipped out of the now open cylinder 50 of the outer capsule 5 and onto a sterile support.

FIG. 11B→step 2: The plug-type extension 33 with the external polygon protrudes from the ampoule 4. To attach a screwing-in instrument, e.g. a ratchet or a dental handpiece 79, a ratchet coupling 7 or a coupling 7 for the dental handpiece is provided. The couplings 7 are provided with a socket 70 complementary to the outer contour 330 on the plug-type extension 33.

FIG. 11C→step 3: If a ratchet is provided as screwing-in instrument, a ratchet coupling 7 is fitted onto the plug-type extension 33 which protrudes above the holding portion 40 from the ampoule 4.

FIG. 11D→step 4: With the ratchet coupling 7 or a coupling piece 7 for motorized drive attached to the plug-type extension 33, the arrangement of implant 1, transfer cap 2 and adapter 3 is removed from the ampoule 4 and transferred to the site of application.

FIGS. 12A through 12M

The following series of figures is used to explain the subsequent step-by-step handling of the arrangement with implant 1, transfer cap 2 and adapter 3, up to the time of production of the master model and beyond this. The example again concerns dental implant technology.

FIG. 12A→step 5: With the ratchet coupling 7 attached to the adapter 3, the implant 1 together with the locked-on transfer cap 2 is screwed into the bone. In general, the implant 1 is first turned gently by hand into the blind bore in the jaw bone before the screwing-in instrument (not shown) is applied.

FIG. 12B→step 6: The implant 1 is screwed into the bone until the intended depth is reached.

FIG. 12C→step 7: After screwing has been completed, the ratchet coupling 7 is removed from the adapter 3.

FIG. 12D→step 8: The adapter 3 has been removed from the inserted implant 1 with the still locked-on transfer cap 2 remaining thereon, counter to the resistance of the frictional connection and counter to the possible additional force-fit engagement between transfer cap 2 and adapter 3.

FIG. 12E→step 9: The axial passage 20 into the transfer cap 2, which axial passage 20 is open at the top and opens out on the top face of the retention wing 28 when the adapter 3 is withdrawn, is closed off with a sealing medium 90.

FIG. 12F→step 10: For impression-taking, an impression tray 9 filled with impression compound 91 is placed over the inserted implant 1, with the transfer cap 2 still locked on the latter.

FIG. 12G→step 11: The impression tray 9 is removed from the inserted implant 1, the transfer cap 2 remaining embedded in the impression compound 91 in the impression tray 9. Upon removal of the impression tray 9, the elastic lip 26 of the transfer cap 2 opens and springs over the shoulder edge 110 of the implant 1. The impression AD is taken and appears as such in the impression tray 9.

FIG. 12H→step 12: A manipulation implant 8 complementary to the inserted implant 1 is made ready. The manipulation implant 8 likewise has a shoulder 811, a shoulder edge 810 and an undercut 83, in the same way as the implant shoulder 11, the shoulder edge 110 and the undercut 13 are present on the original implant 1.

FIG. 12I→step 13: The complementary manipulation implant 8 is fitted into the transfer cap 2, remaining in the impression tray 9, and the impression AD which has been taken. Here once again the lip 26 locks over the shoulder edge 810 on the manipulation implant 8 and engages in the latter's undercut 83.

FIG. 12J→step 14: The impression AD, with the manipulation implant 8 fitted in it, is filled with a modeling compound 92, usually plaster.

FIG. 12K→step 15: The impression tray 9, with the transfer cap 2 embedded therein, is detached from the manipulation implant 8 with the modeling compound 92 which has set around the latter. Around the manipulation implant 8, the master model MM has been obtained which corresponds to the geometric situation in the patient's mouth.

FIG. 12L→step 16: The transfer cap 2 embedded in impression compound 91 is removed from the impression tray 9 and is fitted onto the manipulation implant 8 fitted in the master model MM.

FIG. 12M→step 17: For further processing, the retention wing 28 is detached from the transfer cap 2 fitted on the manipulation implant 8.

The sequence described in FIGS. 12D through 12M can also be used for producing a superstructure for dental bridges and bars which bear on more than one inserted implant 1. Before the impression-taking, the adapter 3 was removed from the combination of implant 1, transfer cap 2 and adapter 3, and the then exposed axial passage 20 in the transfer cap 2 open at the top, and opening out on the top face of the retention wing 28, is sealed off with a sealing medium 90 (see FIGS. 12D through 12F).

The arrangement according to the invention is also advantageous in cases where there are several inserted implants 1 for bars or bridges. The steps following step 17 and intended for production of a prosthetic superstructure will be obvious to the skilled person. The adjoining transfer caps 2 which sit on the manipulation implants 8 anchored in the master model MM are bridged by a bar framework made of plastic that can be burned out, and the composite is removed from the manipulation implants 8. This composite of transfer caps 2 and bar framework is then introduced into an embedding compound. After heating the embedding compound, a cavity is formed which, cast with titanium or gold for example, corresponds to the final bar framework which, after the customary surface treatment, is fitted onto the implants 1 arranged in the patient's mouth.

FIGS. 13A through 13G

This sequence of figures is used to explain the operative handling with the modified arrangement according to FIG. 6A, which handling is in principle the same, so that, in the drawing, introductory steps and intermediate steps can be left out.

FIG. 13A→step 4: The implant 1, with the locked-on transfer cap 2, was removed from a container (not shown) using a ratchet coupling 7 attached to the adapter 3 or using a coupling piece 7 for a motor-driven handpiece 79. The socket 70 grips the plug-type extension 33 of the adapter 3.

FIG. 13B→step 5: The implant 1 is screwed into the bone, for example with the ratchet coupling 7 attached to the adapter 3. The rotation movement is transmitted from the socket 70 to the implant 1 by the driving action of the adapter 3 which, with its inner contour 302, engages with a form-fit on the external polygon 101 of the implant 1.

FIG. 13→step 7: The implant 1 has been screwed into the bone to the desired depth (step 6) and the ratchet coupling 7 has been removed from the adapter 3.

FIG. 13D→step 10: For impression-taking, an impression tray filled with impression compound 91 is fitted over the inserted implant 1, with the locked-on transfer cap 2 and the adapter 3 fitted therein. The transfer cap 2 with its retention wing 28 and the plug-type extension 33 of the adapter 3 are embedded in impression compound 91. Removal of the adapter 3 (step 8) and closure of the inlet opening (step 9) into the transfer cap 9 are not carried out here.

FIG. 13E→step 11: The impression tray with the impression compound 91 is removed from the inserted implant 1, whose external polygon 101 is thereby exposed. The transfer cap 2 with the adapter 3 remains in the impression compound 91 in the impression tray. The impression AD is taken.

FIG. 13F→step 13: In intermediate step 12, a manipulation implant 8 was brought to the transfer cap 2 remaining in the impression compound 91 and it is now locked in this.

FIG. 13G→step 15: In intermediate step 14, the impression AD, in which the manipulation implant 8 complementary to the implant 1 with external polygon 101 fits, was filled with modeling compound 92. After the impression tray with the transfer cap 2 and the adapter 3 fitted therein were removed from the manipulation implant 8, the master model MM for the subsequent dental procedure was obtained. The manipulation implant 8 has a polygon 812, corresponding to the external polygon 101 of the implant 1, and the complementary analogous shoulder 811.

When providing a prosthesis on an inserted implant 1 for an individual artificial tooth, it is necessary to transfer the rotation position between the inserted implant 1, with possible abutment, and the surrounding geometry of the mouth. For this purpose, in a deviation from the method sequence first described according to FIGS. 12C through 12M, the adapter 3 for impression-taking is left in the transfer cap 2 and implant 1, is embedded in the impression tray 9, and is used for the subsequent steps in the production of the master model MM.

The invention claimed is:

1. An assembly for handling a bone implant of the type having a head and a root portion extending from the head, the implant head having a driving structure, an outer implant shoulder, a shoulder edge located beneath the implant shoulder, and an undercut beneath the shoulder edge, said assembly comprising:

an adapter having a driving section which is intended to engage said driving structure on the implant and a plug-type extension for attachment of an instrument; and a transfer cap which can be fitted onto the implant in a releasable manner, said transfer cap having a contact surface complementary to the implant shoulder and an elastic lip for gripping under the shoulder edge and engaging the undercut and an axial passage through which the adapter reaches to the implant, whereby, when the transfer cap is fitted on the implant and the adapter is plugged in, the driving section of the adapter comes in to engagement with said driving structure, and the adapter extends through the axial passage, with the plug-type extension of the adapter protruding from the transfer cap, wherein the adapter, passing through the axial passage, and the transfer cap are connected to one another in a releasable manner thereby forming a releasable connection; and the release force for severing the connection between implant and transfer cap is greater than the release force for severing the connection between transfer cap and adapter.

2. The assembly as claimed in claim 1, wherein for the releasable connection between transfer cap and adapter:

the transfer cap has an inner portion and the adapter has a holding section which engage with one another in a frictional connection.

3. The assembly as claimed in claim 2, wherein for the releasable connection between transfer cap and adapter:

the transfer cap has an elastically deformable contour and the adapter has a mating contour complementary to the latter, and these engage with one another in a force-fit connection.

4. The assembly as claimed in claim 3, wherein
the inner portion on the transfer cap is a cylindrical inner wall;
the holding section on the adapter is a cylinder portion;
the deformable contour on the transfer cap is a bead which narrows the axial passage; and
the mating contour on the adapter is a radial groove into which the bead locks.

5. The assembly as claimed in claim 4, wherein for the releasable connection between transfer cap and adapter:
the inner portion and the holding section for the frictional connection and the deformable contour and the mating contour for the force-fit connection are jointly present.

6. The assembly as claimed in claim 5, wherein
the inner portion on the transfer cap is a cylindrical inner wall;
the holding section on the adapter is a cylinder portion;
the deformable contour on the transfer cap is a bead which narrows the axial passage; and
the mating contour on the adapter is a radial groove into which the bead locks.

7. An assembly for handling a bone implant of the type having a head and a root portion extending from the head, the implant head having a driving structure, an outer implant shoulder, a shoulder edge located beneath the implant shoulder, and an undercut beneath the shoulder edge, said assembly comprising:
an adapter having a driving section which is intended to engage said driving structure on the implant and a plug-type extension for attachment of an instrument; and
a transfer cap which can be fitted onto the implant in a releasable manner, said transfer cap having
a contact surface complementary to the implant shoulder and an elastic lip for gripping under the shoulder edge and engaging the undercut and
an axial passage through which the adapter reaches to the implant,
whereby, when the transfer cap is fitted on the implant and the adapter is pluged in, the driving section of the adapter comes in to engagement with said driving structure, and the adapter extends through the axial passage, with the plug-type extension of the adapter protruding from the transfer cap,
wherein the adapter, passing through the axial passage, and the transfer cap are connected to one another in a releasable manner, and further comprising
a ratchet coupling connected to the adapter in a releasable manner, the release force for severing the connection between the coupling and the adapter being smaller than the release force for severing the connection between implant and transfer cap and smaller than the release force for severing the connection between transfer cap and adapter.

8. An assembly for handling a bone implant of the type having a head and a root portion extending from the head, the implant head having a driving structure, an outer implant shoulder, a shoulder edge located beneath the implant shoulder, and an undercut beneath the shoulder edge, said assembly comprising:
an adapter having a driving section which is intended to engage said driving structure on the implant and a plug-type extension for attachment of an instrument; and
a transfer cap which can be fitted onto the implant in a releasable manner, said transfer cap having
a contact surface complementary to the implant shoulder and an elastic lip for gripping under the shoulder edge and engaging the undercut and
an axial passage through which the adapter reaches to the implant,
whereby, when the transfer cap is fitted on the implant and the adapter is pluged in, the driving section of the adapter comes in to engagement with said driving structure, and the adapter extends through the axial passage, with the plug-type extension of the adapter protruding from the transfer cap,
wherein a non-rotationally symmetrical inner contour in the implants is an internal polygon, or the alternatively provided outer contour on the implant is an external polygon,
in the case where an inner contour is present in the implant, the driving section on the adapter is an external polygon. e.g. an octagon, or
in the case where an outer contour is alternatively present on the implant, the driving section on the adapter is an internal polygon, e.g. an octagon,
The plug-type extension on the adapter is an external polygon,
the implant underneath the shoulder edge narrows in a trumpet shape toward the root portion, by which means the undercut is formed,
the implant shoulder has an inclination in the region of 30°,
the root portion is provided with an external thread, and
in the case where an inner contour is present on the implant, or in the case where alternatively an outer contour is provided on the implant, an internally threaded portion can be arranged within a blind hole,
wherein said external thread is self-tapping.

9. An assembly for handling a bone implant of the type having a head and a root portion extending from the head, the implant head having a driving structure, an outer implant shoulder, a shoulder edge located beneath the implant shoulder, and an undercut beneath the shoulder edge, said assembly comprising:
an adapter having a driving section which is intended to engage said driving structure on the implant and a plug-type extension for attachment of an instrument; and
a transfer cap which can be fitted onto the implant in a releasable manner, said transfer cap having
a contact surface complementary to the implant shoulder and an elastic lip for gripping under the shoulder edge and engaging the undercut and
an axial passage through which the adapter reaches to the implant,
whereby, when the transfer cap is fitted on the implant and the adapter is pluged in, the driving section of the adapter comes in to engagement with said driving structure, and the adapter extends through the axial passage, with the plug-type extension of the adapter protruding from the transfer cap, wherein the combination of the implant, the transfer cap fitted onto the implant, and the adapter extending through the transfer cap, is arranged for operative application in a sterile container, releasable from a fixed position, and
the plug-type extension for gripping by means of an instrument, such as a is positioned accessibly and further comprising a coupling part already connected to the plug-type extension.

10. An assembly for handling a bone implant of the type having a head and a root portion extending from the head, the implant head having a driving structure, an outer implant shoulder, a shoulder edge located beneath the implant shoulder, and an undercut beneath the shoulder edge, said assembly comprising:

an adapter having a driving section which is intended to engage said driving structure on the implant and a plug-type extension for attachment of an instrument; and a transfer cap which can be fitted onto the implant in a releasable manner, said transfer cap having a contact surface complementary to the implant shoulder and an elastic lip for gripping under the shoulder edge and engaging the undercut and an axial passage through which the adapter reaches to the implant, whereby, when the transfer cap is fitted on the implant and the adapter is pluged in, the driving section of the adapter comes in to engagement with said driving structure, and the adapter extends through the axial passage, with the plug-type extension of the adapter protruding from the transfer cap, wherein the implant underneath the shoulder edge narrows in a trumpet shape toward the root portion, by which means the undercut is formed;

the implant shoulder has an inclination in the region of 30°;

the root portion is provided with an external thread; and in the case where an inner contour is present on the implant, or in the case where alternatively an outer contour is provided on the implant, an internally threaded portion can be arranged within a blind hole.

* * * * *

UNITED STATES PATENT AND TRADEMARK OFFICE
CERTIFICATE OF CORRECTION

| | | |
|---|---|---|
| PATENT NO. | : 7,207,801 B2 | Page 1 of 1 |
| APPLICATION NO. | : 10/472494 | |
| DATED | : April 24, 2007 | |
| INVENTOR(S) | : Vogt et al. | |

It is certified that error appears in the above-identified patent and that said Letters Patent is hereby corrected as shown below:

On the Title page, second column under FOREIGN PATENT DOCUMENTS:

"DE    19731073    7/1997"

should read

-- DE    19731673    2/1999--

Signed and Sealed this

Twenty-third Day of October, 2007

JON W. DUDAS
*Director of the United States Patent and Trademark Office*